(12) United States Patent
Oram et al.

(10) Patent No.: US 11,597,905 B2
(45) Date of Patent: Mar. 7, 2023

(54) CELL CULTURE AND TISSUE ENGINEERING SYSTEMS WITH CONTROLLED ENVIRONMENTAL ZONES

(71) Applicant: Octane Biotech Inc., Kingston (CA)

(72) Inventors: Guy Oram, Kingston (CA); Taylor Plant, Kingston (CA); Ian Grant, Kingston (CA); Timothy Smith, Kingston (CA)

(73) Assignee: OCTANE BIOTECH INC., Kingston (CA)

( * ) Notice: Subject to any disclaimer, the term of this patent is extended or adjusted under 35 U.S.C. 154(b) by 143 days.

(21) Appl. No.: 16/727,367

(22) Filed: Dec. 26, 2019

(65) Prior Publication Data

US 2020/0208095 A1 Jul. 2, 2020

Related U.S. Application Data

(60) Provisional application No. 62/785,998, filed on Dec. 28, 2018.

(51) Int. Cl.
*C12M 1/02* (2006.01)
*C12M 3/00* (2006.01)
*C12M 1/36* (2006.01)

(52) U.S. Cl.
CPC ............ *C12M 41/22* (2013.01); *C12M 21/08* (2013.01); *C12M 23/42* (2013.01); *C12M 41/48* (2013.01)

(58) Field of Classification Search
CPC ...... C12M 41/22; C12M 21/08; C12M 23/42; C12M 41/48
See application file for complete search history.

(56) References Cited

U.S. PATENT DOCUMENTS

| 4,642,120 A | 2/1987 | Nevo et al. |
| 4,939,151 A | 7/1990 | Bacehowski et al. |
| 5,041,138 A | 8/1991 | Vacanti et al. |
| 5,081,036 A | 1/1992 | Familletti |

(Continued)

FOREIGN PATENT DOCUMENTS

| AU | 2002/324169 A1 | 3/2003 |
| DE | 4021123 A1 | 4/1991 |

(Continued)

OTHER PUBLICATIONS

Andris et al., "Naïve T Cells are Resistant to Anergy Induction by Anti-CD3 Antibodies," The Journal of Immunology (2004) 173(5):3201-3208.

(Continued)

*Primary Examiner* — William H. Beisner
*Assistant Examiner* — Danielle B Henkel
(74) *Attorney, Agent, or Firm* — Medler Ferro Woodhouse & Mills PLLC

(57) ABSTRACT

An automated cell culture and tissue engineering system comprising defined and separate environmental zones provide for increased control and maintenance of the internal environment of the system such that the temperature, air flow and gases surrounding the bioreactor module form one zone that is maintained separately to a second zone formed surrounding the reagent fluid reservoir. The system further comprises means for elimination and/or management of condensation within the second zone of the system.

15 Claims, 11 Drawing Sheets

(56) References Cited

U.S. PATENT DOCUMENTS

| | | | |
|---|---|---|---|
| 5,240,854 A | 8/1993 | Berry et al. |
| 5,246,699 A | 9/1993 | Debre et al. |
| 5,424,209 A | 6/1995 | Kearney |
| 5,549,134 A | 8/1996 | Browne et al. |
| 5,688,687 A | 11/1997 | Palsson et al. |
| 5,728,581 A | 3/1998 | Schwartz et al. |
| 5,786,207 A | 7/1998 | Katz et al. |
| 5,792,603 A | 8/1998 | Dunkelman et al. |
| 5,827,729 A | 10/1998 | Naughton et al. |
| 5,842,477 A | 12/1998 | Naughton et al. |
| 5,846,828 A | 12/1998 | Peterson et al. |
| 5,882,929 A | 3/1999 | Fofonoff et al. |
| 5,891,455 A | 4/1999 | Sittinger et al. |
| 5,902,741 A | 5/1999 | Purchio et al. |
| 5,906,934 A | 5/1999 | Grande et al. |
| 5,922,604 A | 7/1999 | Stapleton et al. |
| 5,928,936 A | 7/1999 | Ingram |
| 5,989,913 A | 11/1999 | Anderson et al. |
| 5,994,129 A | 11/1999 | Armstrong et al. |
| 6,048,721 A | 4/2000 | Armstrong et al. |
| 6,048,722 A | 4/2000 | Farb et al. |
| 6,060,306 A | 5/2000 | Flatt et al. |
| 6,121,042 A | 9/2000 | Peterson et al. |
| 6,228,635 B1 | 5/2001 | Armstrong et al. |
| 6,238,908 B1 | 5/2001 | Armstrong et al. |
| 6,297,046 B1 | 10/2001 | Smith et al. |
| 6,323,146 B1 | 11/2001 | Pugh et al. |
| 7,348,175 B2 | 5/2008 | Vilendrer et al. |
| 8,492,140 B2 | 7/2013 | Smith et al. |
| 8,727,132 B2 | 5/2014 | Miltenyi et al. |
| 9,499,780 B2 | 11/2016 | Smith et al. |
| 9,534,195 B2 | 1/2017 | Smith et al. |
| 9,701,932 B2 | 7/2017 | Smith et al. |
| 9,783,768 B2 | 10/2017 | Larcher et al. |
| 11,208,626 B2 | 12/2021 | Mason et al. |
| 2001/0043918 A1 | 11/2001 | Masini et al. |
| 2002/0009797 A1 | 1/2002 | Wolf et al. |
| 2002/0009803 A1 | 1/2002 | Vajta |
| 2002/0025547 A1 | 2/2002 | Rao |
| 2002/0037580 A1 | 3/2002 | Schoeb |
| 2002/0038550 A1 | 4/2002 | Adelbert |
| 2002/0146816 A1 | 10/2002 | Vellinger et al. |
| 2002/0155487 A1 | 10/2002 | Greenberger et al. |
| 2003/0032071 A1 | 2/2003 | Wang et al. |
| 2003/0040104 A1 | 2/2003 | Barbera-Guillem |
| 2003/0054335 A1 | 3/2003 | Taya et al. |
| 2003/0159946 A1 | 8/2003 | Eden et al. |
| 2003/0215935 A1 | 11/2003 | Coon |
| 2004/0048364 A1 | 3/2004 | Trosch |
| 2005/0064465 A1 | 3/2005 | Dettloff et al. |
| 2005/0130297 A1 | 6/2005 | Sarem et al. |
| 2005/0186671 A1 | 8/2005 | Cannon et al. |
| 2006/0194193 A1* | 8/2006 | Tsuruta ............... C12M 29/10 435/4 |
| 2014/0087455 A1 | 3/2014 | Kobayashi et al. |
| 2017/0096627 A1 | 4/2017 | Smith et al. |
| 2018/0340142 A1* | 11/2018 | Liu ..................... C12M 29/00 |
| 2019/0049343 A1* | 2/2019 | Kei ..................... G02B 21/32 |
| 2019/0169572 A1 | 6/2019 | Shi et al. |

FOREIGN PATENT DOCUMENTS

| | | |
|---|---|---|
| EP | 0248675 A1 | 12/1987 |
| GB | 1356794 A | 6/1974 |
| JP | 2-119772 A | 5/1990 |
| JP | 2-174848 A | 7/1990 |
| JP | 3-500847 A | 2/1991 |
| JP | 5-503418 A | 6/1993 |
| JP | 6-54678 A | 3/1994 |
| JP | 6-261736 A | 9/1994 |
| JP | 7-501206 A | 2/1995 |
| JP | H08-56646 A | 3/1996 |
| JP | H11-507229 A | 6/1999 |
| JP | 2001-275659 A | 10/2001 |
| JP | 2001-517428 A | 10/2001 |
| JP | 2002-500004 A | 1/2002 |
| WO | 91/05849 A1 | 5/1991 |
| WO | 93/03142 A1 | 2/1993 |
| WO | 1997/12960 A2 | 4/1997 |
| WO | 99/33951 A1 | 7/1999 |
| WO | 99/47922 A2 | 9/1999 |
| WO | 2000/046349 A1 | 8/2000 |
| WO | 01/02030 A2 | 1/2001 |
| WO | 2001/000783 A2 | 1/2001 |
| WO | 2002/028996 A1 | 4/2002 |
| WO | 02/088295 A1 | 11/2002 |
| WO | 03/022985 A2 | 3/2003 |
| WO | 03/087292 A2 | 10/2003 |
| WO | 2003/085101 A1 | 10/2003 |
| WO | 2015/162211 A1 | 10/2015 |
| WO | 2018035182 A1 | 2/2018 |
| WO | 2018/136566 A1 | 7/2018 |

OTHER PUBLICATIONS

Atkuri et al., "Culturing at atmospheric oxygen levels impacts lymphocyte function," PNAS (2005) 102(10):3756-3759.

Austyn et al., "T cell activation by anti-CD3 antibodies: function of Fc receptors on B cell blasts, but not resting B cells, and CD18 on the responding T cells." European Journal of Immunology (1987) 17(9):1329-1335.

Avgoustiniatos et al., "Commercially Available Gas-Permeable Cell Culture Bags May Not Prevent Anoxia in Cultured or Shipped Islets," Transplant Proc. (2008) 40(2):395-400.

Baroja et al., "The anti-T cell monoclonal antibody 9.3 (Anti-CD28) provides a helper signal and bypasses the need for accessory cells in T Cell activation with immobilized anti-CD3 and mitogens," Cellular Immunology (1989) 120(1):205-217.

Berdeja et al., "First-in-human multicenter study of bb2121 anti-BCMA CAR T-cell therapy for relapsed/refractory multiple myeloma: Updated results," Journal of Clinical Oncology (2017) 35(15):3010.

Bohnenkamp et al., "Bioprocess development for the cultivation of human T-lymphocytes in a clincal scale," Cytotechnology (2002) 38:135-145.

Carpenter et al., "Non-Fc Receptor-Binding Humanized Anti-CD3 Antibodies Induce Apoptosis of Activated Human T Cells," The Journal of Immunology (2000) 165(11):6208-6213.

Ceuppens et al., "T cell unresponsiveness to the mitogenic activity of OKT3 antibody results from a deficiency of monocyte Fc gamma receptors for murine IgG2a inability to cross-link the T3-Ti complex," The Journal of Immunology (1985) 135(6):3882-3886.

Chai et al., "Immobilized anti-CD3 mAb induces anergy in murine naïve and memory CD4+ T cells in vitro.," Int Immunol. (1997) 9(7):935-944.

Charron et al., "Monocyte:T cell interaction regulates human T cell activation through a CD28/CD46 crosstalk," Immunol Cell Biol. (2015) 93(9):796-803.

Church et al., "Tumor-specific CD4+ T cells maintain effector and memory tumor-specific CD8+ T cells," European Journal of Immunology (2014) 44:69-79.

Clavreul et al., "Interelationship between CD3 and CD28 pathways in a murine T cell thymoma," Molecular Immunology (2000) 37(10):571-577.

Dudley et al., "Generation of Tumor-Infiltrating Lymphocyte Cultures for Use in Adoptive Transfer Therapy for Melanoma Patients," J Immunother. (2003) 26(4):332-342.

Fathman et al., "Molecular mechanisms of CD4+ T-cell anergy," Nature Reviews Immunology (2007) 7:599-609.

FDA, Available online at: https://www.fda.gov/downloads/AdvisoryCommittees/CommitteesMeetingMaterials/Drugs/OncologicDrugsAdvisoryCommittee/UCM566166.pdf.

FDA, Regenerative Medicine Advanced Therapy Designation. (2017). Available at: https://www.fda.gov/BiologicsBloodVaccines/CellularGeneTherapyProducts/ucm537670.htm. (Accessed: Aug. 8, 2017).

FDA, Sepax Cell Separation System and single use kits. (2011). Available at: https://www.fda.gov/downloads/BiologicsBloodVaccines/BloodBloodProducts/ApprovedProducts/

(56) References Cited

OTHER PUBLICATIONS

SubstantiallyEquivalent510kDeviceInformation/UCM278385.pdf. (Accessed: Nov. 8, 2017).
Feldmann et al., "Novel humanized and highly efficient bispecific antibodies mediate killing of prostate stem cell antigen-expressing tumor cells by CD8+ and CD4+ T cells," J Immunol. (2012) 189(6):3249-3259.
Fleischer et al., "Differential expression and function of CD80 (B7-1) and CD86 (B7-2) on human peripheral blood monocytes," Immunology (1996) 89(4):592-598.
Gottschalk et al., The hype, hope and reality of personalization. The Medicine Maker (2015) p. 38-41.
Greenwald et al., "The B7 Family Revised," Annual Review of Immunology (2005) 23:515-548.
Grishagin, Ivan V., "Automatic cell counting with ImageJ," Analytical Biochemistry (2015) 473:63-65.
Hammill et al., "Designed ankyrin repeat proteins are effective targeting elements for chimeric antigen receptors," Journal for ImmunoTherapy of Cancer (2015) 3(55):1-11.
Harding et al., "CD28-mediated signalling co-stimulates murine T cells and prevents induction of anergy in T-cell clones," Nature (1992) 356:607-609.
Hasegawa et al., "In vitro Stimulation of CD8 and CD4 T Cells by Dendritic Cells Loaded with a Complex of Cholesterol-Bearing Hydrophobized Pullulan and NY-ESO-1 Protein: Identification of a New HLA-DR15-Binding CD4 T-Cell Epitope," Clinical Cancer Research (2006) 12(6):1921-1927.
Hollyman et al., "Manufacturing validation of biologically functional T cells targeted to CD19 antigen for autologous adoptive cell therapy," J Immunother. (2009) 32(2):169-180.
Ju et al., "A functional anti-human 4-1BB ligand monoclonal antibody that enhances proliferation of monocytes by reverse signaling of 4-1BBL," Hybrid Hybridomics (2003) 22(5):333-338.
Kaiser et al., "Towards a commercial process for the manufacture of genetically modified T cells for therapy," Cancer Gene Therapy (2015) 22:72-78.
Kalos et al., "T Cells with Chimeric Antigen Receptors Have Potent Antitumor Effects and Can Establish Memory in Patients with Advanced Leukemia," Sci Transl Med. (2011) 3(95):1-21.
Kebriaei et al., "Phase I trials using *Sleeping Beauty* to generate CD19-specific CAR T cells," The Journal of Clinical Investigation (2016) 126(9):3363-3376.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," Journal of Clinical Oncology (2016 33(6):540-549.
Lafferty et al., "A new analysis of allogeneic interactions," Aust J Exp Biol Med Sci. (1975) 53(1):27-42.
Laux et al., "Response Differences between Human CD4+ and CD8+ T-Cells during CD28 Costimulation: Implications for Immune Cell-Based Therapies and Studies Related to the Expansion of Double-Positive T-Cells during Aging," Clinical Immunology (2000) 96(3):187-197.
Ledbetter et al., "CD28 Ligation in T-cell Activation: Evidence for Two Signal Transduction Pathways," Blood (1990) 75(7):1531-1539.
Levine et al., "Global Manufacturing of CAR T Cell Therapy," Molecular: Therapy: Methods & Clinical Development (2017) 4:92-101.
Li et al., "Comparison of anti-CD3 and anti-CD28-coated beads with soluble anti-CD3 for expanding human T cells: Differing impact on CD8 T cell phenotype and responsiveness to restimulation," Journal of Translational Medicine (2010) 8(104):1-15.
Lock et al., "Automated Manufacturing of Potent CD20-Directed Chimeric Antigen Receptor T Cells for Clinical Use," Human Gene Therapy (2017) 28(10):914-925.

Locke et al., "Abstract CT019: Primary results from ZUMA-1: a pivotal trial axicabtagene ciloleucel (axicel; KTE-C19) in patients with refractory aggressive non-Hodgkin lymphoma (NHL)," Cancer Research (2017) 77(13).
Locke et al., "Phase 1 Results of ZUMA-1: A Multicenter Study of KTE-C19 Anti-CD19 CAR T Cell Therapy in Refractory Aggressive Lymphoma," Molecular Therapy (2017) 25(1):285-295.
Lu et al., "A Rapid Cell Expansion Process for Production of Engineered Autologous CAR-T Cell Therapies," Human Gene Therapy Methods (2016) 27(6):209-218.
Lu et al., "Automated dynamic fed-batch process and media optimization for high productivity cell culture process development," Biotechnology and Bioengineering (2013) 110(1):191-205.
Lu et al., "Treatment of Patients with Metastatic Cancer Using a Major Histocompatibility Complex Class II-Restricted T-Cell Receptor Targeting the Cancer Germline Antigen MAGE-A3," Journal of Clinical Oncology (2017) 35(29):3322-3329.
Mock et al., "Automated manufacturing of chimeric antigen receptor T cells for adoptive immunotherapy using CliniMACS Prodigy," Cytotherapy (2016) 18(8):1002-1011.
Morrissey et al., "End-to-End Cell Therapy Automation: An Immunotherapy Case Study," BioPharm International (2017) 2:10-18.
Nilsson et al., "Optimal Blood Mononuclear Cell Isolation Procedures for Gamma Interferon Enzyme-Linked Immunospot Testing of Healthy Swedish and Tanzanian Subjects," Clinical and Vaccine Immunology (2008) 15(4):585-589.
Nociari et al., "A novel one-step, highly sensitive fluorometric assay to evaluate cell-mediated cytotoxicity," Journal of Immunological Methods (1998) 213(2):157-167.
Odeleye et al., "On the fluid dynamics of a laboratory scale single-use stirred bioreactor," Chemical Engineering Science (2014) 111(100):299-312.
Reusch et al., "A tetravalent bispecific TandAb (CD19/CD3), AFM11, efficiently recruits T cells for the potent lysis of $CD19^+$ tumor cells," MAbs (2015) 7(3):584-604.
Riddell et al., "Adoptive Therapy with Chimeric Antigen Receptor Modified T Cells of Defined Subset Composition," Cancer J (2014) 20(2):141-144.
Riddell et al., "The use of anti-CD3 and anti-CD28 monoclonal antibodies to clone and expand human antigen-specific T cells," Journal of Immunological Methods (1990) 128(2):189-201.
Romagnani, S, "Type 1 T helper and type 2 T helper cells: functions, regulation and role in protection and disease," Int J Clin Lab Res (1991) 21(2):152-158.
Schwartz, RH, "A cell culture model for T lymphocyte clonal anergy," Science (1990) 248(4961):1349-1356.
Schwartz, RH, "T cell anergy," Annu Rev Immunol. (2003) 21:305-334.
Tangying et al., "A Rapid Cell Expansion Process for Production of Engineering Autologous CAR-T Cell Therapies," Human Gene Therapy Methods (2016) 27(6):209-218.
Tax et al., "Polymorphism in mitogenic effect of IgG1 monoclonal antibodies against T3 antigen on human T cells," Nature (1983) 304(5925):445:447.
Trainor et al., "Rethinking clinical delivery of adult stem cell therapies," Nature Biotechnology (2014) 32:729-735.
Trickett et al., "T cell stimulation and expansion using anti-CD3/CD28 beads," Journal of Immunological Methods (2003) 275(1-2):251-255.
Tuefferd et al., "HER2 Status in Ovarian Carcinomas: A Multicenter GINECO Study of 320 Patients," PLoS ONE (2007) 11:e1138.
Turtle et al., "CD19 CAR-T cells of defined $CD4^+$ :$CD8^+$ composition in adult B cell ALL patients," The Journal of Clinical Investigation (2016) 126(6):2123-2138.
Vanseggelen et al., "Chimeric antigen receptor-engineered T cells as oncolytic virus carriers," Molecular Therapy—Oncolytics (2015) 150014.
Verwilghen et al., "Differences in the stimulating capacity of immobilized anti-CD3 monoclonal antibodies: variable dependence

(56) References Cited

OTHER PUBLICATIONS on interleukin-1 as a helper signal for T-cell activation," Immunology (1991) 72:269-276.
Wang et al., "Clinical manufacturing of CAR T cells: foundation of a promising therapy" Mol. Ther.—Oncolytics (2016) 3:16015.
Wang et al., "Manufacture of tumor- and virus-specific T lymphocytes for adoptive cell therapies," Cancer Gene Ther. (2015) 22(2):85-94.
Wauwe et al., "OKT3: a monoclonal anti-human T lymphocyte antibody with potent mitogenic properties," The Journal of Immunology (1980) 124(6):2708-2713.
Wegener, C, "Cell Washing with the LOVO Cell Processing System," BioProcess International (2014) p. 78.
Weiss et al., "T cell activation: differences in the signals required for IL 2 production by nonactivated and activated T cells," J Immunol (1985) 135(6):3669-3673.
Wolf et al., "Induction of anergy in resting human T lymphocytes by immobilized anti-CD3 antibodies," European Journal of Immunology (1994) 24(6):1410-1417.
Yan et al., "HER2 expression status in diverse cancers: review of results from 37,992 patients," Cancer Metastasis Rev (2015) 34:157-164.
Zhu et al., "CD137 stimulation delivers an antigen-independent growth signal for T lymphocytes with memory phenotype," Immunobiology (2007) 109(11):4882-4889.
Konstantin B. Konstantinov "Monitoring and Control of the Physiological State of Cell Cultures" Biotechnology and Bioengineering, vol. 52, pp. 271-289 (1996) (Year: 1996).
Farndale "Pulsed Electromagnetic Fields Promote Collagen Production in Bone Marrow Fibroblasts via Athermal Mechanisms" Calcif Tissue Int (1985) 37:178-182.
Shi et al., Performance of Mammalian Cell Culture Bioreactor with a New Impeller Design, Biotechnology and Bioengineering, Jun. 20, 1992, pp. 260-270, vol. 40, John Wiley & Sons, Inc.
Declaration from Mark Selker, Submitted in *Lonza Walkersville, Inc.* v. *Adva Biotechnology LTD.*, United States District Court for the District of Maryland, Case No. 8:20-cv-03099-PX, Jan. 5, 2022.
Declaration from James C. Leung, Submitted in *Lonza Walkersville, Inc.* v. *Adva Biotechnology LTD.*, United States District Court for the District of Maryland, Case No. 8:20-cv-03099-PX, Jan. 7, 2022.

\* cited by examiner

CELL CULTURE AND TISSUE ENGINEERING SYSTEMS WITH CONTROLLED ENVIRONMENTAL ZONES

CROSS-REFERENCE TO RELATED APPLICATIONS

The present application claims benefit of U.S. Provisional Application No. 62/785,998, filed Dec. 28, 2018, the disclosure of which is incorporated by reference herein in its entirety.

FIELD

The invention relates to tissue engineering systems and methods for automated cell culture and tissue engineering that include uniform operational environmental zones to provide more consistent biological processes. Such systems and methods find use in a variety of clinical and laboratory settings.

BACKGROUND

Cell culture automation is a desired trend for providing scalability for mass production, decreasing variability in culture, decreasing risks of culture contamination as well as many economical cost and time frame benefits related to generation of cell or tissue based implants for clinical therapies and cell based assay systems for diagnostic evaluations.

Automated cell culture protocols used for more complex biological processes, such as for example autologous patient treatment, however may be more complex requiring more precise operational control. For autologous patient treatment, successful biological culture is critical and thus each operational aspect must be strictly adherent to a specific protocol. For example, while initial culture media can be programmed for delivery to cell cultures at suitable temperatures such as 37° C., maintaining a strict adherence to this temperature throughout an entire cell culture process that may be days long, proves more difficult. Many currently used automated systems providing cell incubation capability experience thermal challenges such as: trying to achieve and maintain overall thermal uniformity; changes in air temperatures due to external operator access; maintaining refrigerated reagent storage; and the development of condensation within the housing which may lead to potential microbial contamination.

Refrigerated storage of reagents is desired to avoid their deterioration, however, refrigerated reagent storage can negatively affect the thermal performance and stability of the cell bioreactor making it more difficult to maintain the desired elevated temperature required for cell culture. Furthermore, the reduction of the temperature of the storage environment for process reagents to refrigerated temperatures inevitably generates condensation. Condensation forms when the air is chilled below the dew point causing the water vapor in the air to condense into a liquid form, especially on surfaces that are cold relative to the surroundings. Warm, humid air may come into contact with the colder surface of the storage environment when the system is opened to load the reagents. This condensation can be problematic if the volume of condensate results in handling issues or contamination issues within the storage environment.

Gas concentrations can also significantly influence biological performance as gases such as $CO_2$ are used to modulate the pH of active cultures. In the event that the culture system experiences restricted access to the buffering role of delivered $CO_2$, there is the prospect of inhomogeneous pH control across the culture zone. Thus gas concentration uniformity is also required in cell culture and tissue engineering systems.

Accordingly there is still a continual need to improve aspects of automated cell culture and tissue engineering systems such as providing higher fidelity of environmental control within the system.

The discussion of the background herein is included to explain the context of the inventions described herein. This is not to be taken as an admission that any of the material referred to was published, known, or part of the common general knowledge as of the priority date of any of the claims.

SUMMARY

Herein described are cell culture and tissue engineering systems and methods that include uniform operational environments to provide more consistent control over biological processes. Uniform operational environments relating to airflow, temperature, gas control and condensation control are integrated within the systems and methods described herein.

Automated cell culture and tissue engineering systems as described herein are configured to generate, adjust and maintain controlled isolated environmental zones for proper operation of a cell culture cassette and thus the biological process that is underway. Temperatures, humidity levels and gas concentrations are controlled. Temperature fluctuations and humidity variations are minimized.

Surprisingly, two distinct temperature zones are created and maintained in the cassette receiving area of the system where the cell culture cassette is installed and operated. The bioreactor module component of the cassette is retained in a warm zone while the reagents fluid reservoir component is retained in a cold zone during operation of the system. The warm zone comprises a re-circulating warm high airflow path surrounding the bioreactor module that is generated by an adjacent separate heating assembly. The warm circulating air also permeates the culture aspect of the cassette through ventilation slots. This is similar in concept to the slots in the reservoir. The cold zone comprises a circulating cold ducted airflow path that both surrounds and partially penetrates (flows through) a portion of the reagents fluid reservoir. The cold airflow path is generated by an adjacent cold thermal assembly. The cold zone also contains a condensation control means for the control and removal of condensation within the cold zone.

Both the warm zone and cold zone further comprise a segregated independently controlled gas environment. In the warm zone this helps to provide for specific gas concentrations that influence dissolved gases present in cell culture media such as oxygen and carbon dioxide through fluid surface gas exchange. The adjustment and/or maintenance of dissolved gases is influential in terms of biological performance, including aspects such as the delivery of oxygen and the maintenance of a target pH for the cell culture. The control of dissolved gases within the culture media is achieved through the recirculation of culture media across a gas exchange membrane (such as silicone tubing) whereby the concentration of dissolved gases within the culture fluid responds to the concentration gradient between the fluid and the surrounding gaseous environment. By adjusting the environment, the level of dissolved gases within the culture fluid is simultaneously adjusted.

The automated cell culture and tissue engineering system is configured with a movable thermal barrier assembly that, during installation of a cell culture cassette, serves to lock the cassette within the system operational interface and in doing so, forms the warm zone and the cold zone and keeps these two zones thermally and physically separated. Insulating mechanisms are provided to ensure that the warm zone and cold zone are insulated from each other and do not influence either the cell culture or the properties of the stored reagents. The movable thermal barrier assembly creates and defines portions of the borders of each of the warm zone and the cold zone.

The system heating and cooling assemblies, as well as operational robotics are contained/positioned separate to that of the cassette receiving area of the system, which is beneficial not to interfere with warm airflow or cold airflow paths and their function. Further, the heating assembly is segregated to be separate and insulated from the cooling assembly. The system heating assembly is configured to generate and regulate the temperature of the continuous warm high airflow path for several days as is required and further can quickly adjust for any temperature drop that may occur due to the entrance of cooler room temperature air during opening and inspection of the system. The configuration and shape of the system helps to provide for a warm airflow path to be directed solely at the bioreactor module and continually circulate around and through it. The cold thermal assembly is configured to continually remove heat as airflow in the cold zone is continually drawn through a cold thermal assembly and the air temperature is reduced. The cold zone is configured to have a channeled airflow, that is, the cold airflow path follows structural features including airflow channels, airflow baffles and air flow vents to help carry the cooled air through the cold zone around and partially through the reagents fluid reservoir and further through an optional adjacent cold reservoir external to the reagents fluid reservoir. These structural features help to prevent and minimize any blockage of the return air (by filled fluids bags) traveling toward to the cold thermal assembly.

The provision of a separate warm zone and separate cold zone minimizes the amount and location of condensation that may form within the system as the system is only subjected to condensation in the cold zone which has a mechanism to effectively prevent, control and remove condensation.

The invention in aspects comprises an automated cell culture and tissue engineering system that comprises a closed automated cell culture cassette for the one of more of cell source isolation, cell proliferation/expansion, cell differentiation, cell isolation, cell labelling, cell purification, cell washing and cell seeding onto scaffolds for tissue formation (product formation). In aspects, the cells are mammalian. In further aspects, human cells. The type of cell or tissue is not limiting. In one non-limiting example, pluripotent stem cells, such as embryonic stem cells and induced pluripotent stem (iPS) cells, may be cultured and expanded for cell replacement therapy.

The automated cell culture cassette is in aspects a closed, single-use disposable cassette comprising one or more sterile bioreactor modules fluidly connected to a reagent fluids reservoir. The sterile bioreactor is loaded with desired cells and/or tissue and connected to the reagent fluid reservoir which is preloaded to contain the required fluid reagents. The sterility of the cassette is maintained throughout.

The automated cell culture cassette is operatively employed within an automated cell culture and tissue engineering system along with a dedicated software program to deliver and track a desired process(es). Suitable non limiting automated cell culture and tissue engineering systems are described in U.S. Pat. Nos. 8,492,140; 9,701,932; 9,534,195; 9,499,780; and 9,783,768 (the contents of each of these U.S. patents is incorporated by reference in their entireties).

Embedded sensors within the cell culture cassette, provide real-time biofeedback and enable automatic adjustment in bioprocessing to accommodate natural variations in cell source behaviour. The entire bioprocess is contained within the disposable cassette to ensure maximum patient and operator safety and to streamline logistics. Further, in order to successfully support multiple biological steps in a cell process sequence, the cassette bioreactor(s) are integrated in combination with biosensor feedback within one or more interlinked bioreactors, to provide a highly intuitive system with precise control at each cell and tissue stage. This comprehensive level of automation enable technically feasible and economical scale-up, patient-scale cell manufacturing capabilities and allows streamlined production of cell therapies under good manufacturing practice (GMP) conditions thus meeting the unique challenges of different autologous and allogeneic clinical applications of cell and tissue therapy.

Advantageously, the cell culture cassette is installed and operationally retained within the cell culture and tissue engineering system housing in a manner that the bioreactor module resides solely in the distinct warm zone and the reagents fluid reservoir resides solely in a distinct cold zone. The installation of the cell culture cassette into the system is via the actuation and locking of a movable thermal barrier assembly that environmentally isolates the first thermal zone from the second thermal zone with respect to temperature, gases and humidity. The cell culture cassette comprises the bioreactor module with attached reagents fluids reservoir. While this combination into a single cell culture cassette is more user friendly, it poses more of a challenge with respect to creating separate and distinct environmental zones for the bioreactor module and for the reagents fluid reservoir versus a more simplistic design based on physically separate bioreactor module and reservoir that can be located in separate environmental zones.

The invention provides dedicated airway paths within the warm zone and the cold zone ensuring controlled distribution of temperature/gas is provided about the bioreactor module housing the cell culture(s) and about the reagents fluid reservoir in a manner to preclude points of distortions of uniformity in each zone.

In aspects of the invention is a cell culture and tissue engineering system comprising two distinct independent thermal airflows, a first airflow comprising a high velocity warm airflow for directing at and around a bioreactor module of a cell culture cassette, and a second airflow comprising a cold airflow for circulating around and through a reagents fluid reservoir operatively connected to the bioreactor module, wherein said first airflow and said second airflow are separate substantially (these zones in embodiments are not hermetically sealed relative to each other) and cannot intermingle.

In aspects the first airflow and said second airflow are contained within a cell culture cassette receiving area of said system.

In aspects, the cell culture cassette receiving area is separate from operational, heating and cooling assemblies of the system.

In aspects the cell culture cassette receiving area defines a warm zone that comprises the high velocity warm airflow.

In aspects the warm zone comprises substantially homogeneous temperature within the warm zone.

In aspects the cell culture cassette receiving area defines a cold zone that comprises the cold airflow, said cold zone positioned beneath the warm zone.

In aspects the cold zone comprises a means for reducing or eliminating condensation. In aspects a thermal platform separates the warm zone from the cold zone. In aspects, the thermal platform contains seals.

In aspects of the invention is a method for maintaining a controlled thermal environment for biological processes within a bioreactor module of a cell culture cassette, the method comprising:

directing a first airflow comprising a high velocity warm airflow at and around the bioreactor module, and simultaneously circulating a cold air flow around and through a reagents fluid reservoir operatively connected to the bioreactor module, wherein said first airflow and said second airflow are separate and cannot intermingle.

According to an aspect of the invention is a cell culture and tissue engineering system comprising a thermal zone architecture for providing a more consistent and controlled environment for facilitating biological processes, wherein the system comprises:

a distinct warm zone compartment that retains a bioreactor module while continuously circulating a high velocity warm airflow path around and directed at and around the bioreactor module; and a distinct cold zone compartment that retains a reagents fluid reservoir functionally connected to the bioreactor module, while continuously circulating a cold airflow path around and through the reagents fluid reservoir.

In aspects, the distinct cold zone compartment further comprises a means for reducing or eliminating condensation.

In aspects, the warm zone compartment further comprises a distinct gas environment to that of the cold zone compartment.

According to a further aspect of the invention is an automated system for cell culture and tissue engineering that retains a cell culture cassette in two distinct temperature and gas controlled environments, wherein a biological reactor component of the cassette is operatively retained in a substantially homogeneous warm airflow zone with controlled gas concentrations, and wherein a reagents fluid reservoir component of the cassette resides in a substantially homogeneous cold airflow zone, wherein the warm airflow zone is distinctly separated from the cold airflow zone, and wherein the cold airflow zone further comprises a means for preventing or eliminating undesirable moisture accumulation therein.

According to a further aspect of the invention is a cell culture and tissue engineering system for receiving and operationally supporting an automated cell culture cassette in a more consistently controlled environment for biological processes, the cell culture cassette comprising a bioreactor module and a reagents fluid reservoir, the system comprising:

a warm zone configured for circulating a warm airflow path surrounding the bioreactor module;

a cold zone configured for circulating a cold airflow path surrounding the reagents fluid reservoir; and a movable thermal barrier assembly for thermally isolating said warm zone from said cold zone upon installation of the cell culture cassette, and for securing the bioreactor module solely within the warm zone and the reagents fluid reservoir solely within the cold zone.

According to a further aspect of the invention is a cell culture cassette comprising:

a bioreactor module having a bottom part attached with a reagents fluid reservoir;

the reagents fluid reservoir comprising a fluids bag container having open air ducts located on front and back walls of the reservoir.

In aspects, the fluids bag container comprises a roof and floor, the roof comprising baffles extending downwardly.

In aspects, the cassette further comprises a layer of thermal insulation positioned in between the bottom of the bioreactor module and the roof of the fluids bag container, said layer of thermal insulation insulating against migration of heat from the bioreactor module.

In aspects, the reagents fluid reservoir is attached via port connections positioned on the roof of said fluids bag container and unobstructed by said layer of thermal insulation.

In aspects, the reagents fluid reservoir further comprises snap tabs for attaching to the bioreactor module.

According to a further aspect of the invention is a reagents fluid reservoir for connection to a bioreactor module, the reagents fluid reservoir comprising a fluids bag container having open air ducts located on front and back walls of the reservoir.

In aspects, the fluids bag container comprises a roof and floor, the roof comprising baffles extending downwardly.

According to an aspect of the invention is an automated cell culture and tissue engineering system for receiving and operationally supporting an automated cell culture cassette in a more consistently controlled environment for biological processes, the cell culture cassette comprising a bioreactor module and a reagents fluid reservoir, the system comprising:

a warm zone configured for circulating a tangential warm airflow path surrounding the bioreactor module;

a cold zone configured for circulating a tangential cold airflow path surrounding the reagents fluid reservoir; and a movable thermal barrier assembly for thermally isolating said warm zone from said cold zone upon installation of the cell culture cassette, and for securing the bioreactor module solely within the warm zone and the reagents fluid reservoir solely within the cold zone.

In any of the aforementioned aspects, the system and method may comprise one or more controllers and associated software, sensors, and user interface.

Non-limiting aspects are as follows:

1A. A cell culture and tissue engineering system comprising two distinct independent thermal airflows, a first airflow comprising a high velocity warm airflow for directing at and around a bioreactor module of a cell culture cassette, and a second airflow comprising a cold airflow for circulating around and through a reagents fluid reservoir operatively connected to the bioreactor module,
wherein said first airflow and said second airflow are separate and cannot intermingle.

1B. The system of claim 1A, wherein said first airflow and said second airflow are contained within a cell culture cassette receiving area of said system.

1C. The system of claim 1B, wherein said cell culture cassette receiving area defines a warm zone that comprises the high velocity warm airflow.

1D. The system of claim 1C, wherein said warm zone comprises substantially homogeneous temperature within the warm zone.

1E. The system of claim 1B, 1C or 1D, wherein said cell culture cassette receiving area defines a cold zone that comprises the cold airflow, said cold zone positioned beneath the warm zone.

1F. The system of claim 1E, wherein said cold zone comprises a means for reducing or eliminating condensation.

1G. The system of claim 1F, wherein a thermal platform separates the warm zone from the cold zone.

1H. A method for maintaining a controlled thermal environment for biological processes within a bioreactor module of a cell culture cassette, the method comprising:

directing a first airflow comprising a high velocity warm airflow at and around the bioreactor module, and simultaneously circulating a cold air flow around and through a reagents fluid reservoir operatively connected to the bioreactor module, wherein said first airflow and said second airflow are separate and cannot intermingle.

1J. The method of claim 1H using the system of any one of claims 1A to 1H.

2A. A cell culture and tissue engineering system comprising a thermal zone architecture for providing a more consistent and controlled environment for facilitating biological processes, wherein the system comprises:

a distinct warm zone compartment that retains an bioreactor module while continuously circulating a high velocity warm airflow path around and directed at and around the bioreactor module; and a distinct cold zone compartment that retains a reagents fluid reservoir functionally connected to the bioreactor module, while continuously circulating a cold airflow path around and through the reagents fluid reservoir.

2B. The system of claim 2A, wherein the distinct cold zone compartment further comprises a means for reducing or eliminating condensation.

2C. The system of claim 2A or 2B, wherein said warm zone compartment further comprises a distinct gas environment to that of the cold zone compartment.

2D. A method for maintaining a controlled environment for biological processes within a bioreactor and for maintaining fluids required for the bioreactor at a cool temperature for stability, the method comprising the use of the system of any one of claims 2A to 2C.

3A. An automated system for cell culture and tissue engineering that retains a cell culture cassette in two distinct temperature and gas controlled environments, wherein a biological reactor component of the cassette is operatively retained in a substantially homogeneous warm airflow zone with controlled gas concentrations, and wherein a reagents fluid reservoir component of the cassette resides in a substantially homogeneous cold airflow zone, wherein the warm airflow zone is distinctly separated from the cold airflow zone, and wherein the cold airflow zone further comprises a means for preventing or eliminating undesirable moisture accumulation therein.

3B. A method for maintaining a controlled environment for biological processes within a bioreactor and for maintaining fluids required for the bioreactor at a cool temperature for stability, the method comprising the use of the system of claim 3A.

1. A cell culture and tissue engineering system for receiving and operationally supporting an automated cell culture cassette in a more consistently controlled environment for biological processes, the cell culture cassette comprising a bioreactor module and a reagents fluid reservoir, the system comprising:

a warm zone configured for circulating a warm airflow path surrounding the bioreactor module;

a cold zone configured for circulating a cold airflow path surrounding the reagents fluid reservoir; and a movable thermal barrier assembly for thermally isolating said warm zone from said cold zone upon installation of the cell culture cassette, and for securing the bioreactor module solely within the warm zone and the reagents fluid reservoir solely within the cold zone.

2. The cell culture and tissue engineering system of claim 1, wherein said cold zone further comprises a condensation control means for minimizing and eliminating undesirable moisture accumulation therein.

3. The cell culture and/or tissue engineering system of claim 1 or 2, wherein said warm zone and said cold zone each comprise a substantially segregated gas environment.

4. The cell culture and tissue engineering system of claim 1, 2 or 3, said system having a housing comprising an outer shell cover and an inner shell body, wherein the outer shell cover encloses a front opening of the inner shell body in an enveloped manner when the system is closed.

5. The cell culture and tissue engineering system of claim 5, wherein said outer shell cover is connected to the inner shell body for rotation while the inner shell body remains stationary, the outer shell cover rotates along an outer arc of the inner shell body to expose the front opening of the inner shell body for access thereto and stops rotating when the outer shell cover nests the inner shell body.

6. The cell culture and tissue engineering system of claim 4 or 5, wherein said front opening of the inner shell body comprises a periphery with an inflatable sealing means for a sealing engagement with an inside surface of the outer shell body when the system is closed.

7. The cell culture and tissue engineering system of claim 6, wherein said periphery comprises a U shaped channel for retaining said inflatable sealing means.

8. The cell culture and tissue engineering system of claim 7, wherein the sealing means comprises an elastomeric tube that fits within the U shaped channel, the elastomeric tube being substantially flat when the system is open and the sealing means activated upon closing the system to introduce an inflation pressure into the cavity of the inflatable seal causing displacement of the seal to effect a positive seal between the outer shell cover and the front opening of the inner shell body.

10. The cell culture and tissue engineering system of claim 9, wherein said outer shell cover is configured as an arc-shaped body that helps to direct the circulating warm airflow path surrounding the bioreactor module and also helps to direct the circulating cold airflow path surrounding the reagents fluid reservoir.

11. The cell culture and tissue engineering system of claim 10, wherein said arc-shaped body comprises a plurality of thermal cells to act as an exterior thermal barrier.

12. The cell culture and tissue engineering system of any one of claims 4 to 11, wherein the movable thermal barrier assembly is disposed on an operational robotics interface positioned within the front opening of the inner shell body.

13. The cell culture and tissue engineering system of claim 12, wherein said operational robotics interface is connected to associated internal robotics and comprises valve actuators, peristaltic pumps and related control systems for mating with corresponding connections on the cell culture cassette.

14. The cell culture and tissue engineering system of any one of claims 4 to 11, wherein said movable thermal barrier assembly comprises:
a pair of spaced apart levered arms internally connected at either side of the operational robotics interface that support a central thermal platform with an associated upper handrail 15. The cell culture and tissue engineering system of claim 14, wherein said movable thermal barrier assembly is movable from a first raised position for installing the cell culture cassette, to a second lowered position that locks and retains the cell culture cassette against the operational robotics interface for accurate alignment and retention thereto and simultaneously isolating the warm zone from the cold zone.

16. The cell culture and tissue engineering system of claim 15, wherein said upper handrail is sized to closely conform to dimensions of the cell culture cassette and provide a gripping means to lock the cassette into position for operation or to raise the thermal platform.

17. The cell culture and tissue engineering system of claim 14, 15 or 16, wherein recesses are provided on the operational robotics interface adjacent said levered arms for providing operator controlled access to open the assembly.

18. The cell culture and tissue engineering system of any one of claims 14 to 17, wherein said thermal platform extends forward and radiates from around the cell culture cassette to the outer shell cover.

19. The cell culture and tissue engineering system of claim 18, wherein the thermal platform comprises a flexible outer seal at its front outer boundary to accommodate relative motion between the thermal platform and the outer shell cover and a flexible inner seal that is directly adjacent to the cell culture cassette.

20. The cell culture and tissue engineering system of claim 19, wherein the flexible inner seal accommodates mounting tolerances of the cell culture cassette.

21. The cell culture and tissue engineering system of claim 19 or 20, wherein said flexible outer seal and the said flexible inner seal are elastomeric and impermeable to vapor.

22. The cell culture and tissue engineering system of claim 21, wherein said flexible outer seal and the said flexible inner sear are wiper-style seals.

23. The cell culture and tissue engineering system of any one of claims 14 to 22, wherein when in the locked position the thermal platform comprises part of the lower surface boundary of the warm zone and part of the upper surface boundary of the cold zone.

24. The cell culture and tissue engineering system of any one of claims 14 to 18, wherein the inner shell body comprises a floor supporting a tray with forward cantilevered ledge that supports part of a bottom surface of the cell culture cassette.

24a. The cell culture and tissue engineering system of claim 24, wherein an airflow duct is defined by the floor and the tray.

25. The cell culture and tissue engineering system of any one of claims 4 to 24, wherein a heating assembly is provided in an upper section of the inner shell body generates warm air directed at the bioreactor module.

26. The cell culture and tissue engineering system of claim 25, wherein the heating arrangement comprises a high capacity linear fan operably connected to a heated airflow director to generate and direct a high velocity warm airflow path.

27. The cell culture and tissue engineering system of claim 26, wherein the high tangential warm airflow path surrounding the bioreactor module promotes uniformity of temperature of the warm zone and thus of biological processes within the bioreactor.

28. The cell culture and tissue engineering system of claim 27, wherein the high tangential velocity warm airflow path surrounding the bioreactor module helps to maintain the bioreactor internal temperature at about 35° C., at about 36° C., at about 37° C., at about 38° C. or at about 39° C.

28a. The cell culture and tissue engineering system of claim 28, wherein gases are selectively introduced into the warm zone.

28b. The cell culture and tissue engineering system of claim 28a, wherein gases comprise one or more of oxygen, carbon dioxide and nitrogen.

28c. The cell culture and tissue engineering system of claim 28a or 28b, wherein the warm zone comprises sensors in the in the warm airflow path for monitoring the gases.

28d. The cell culture and tissue engineering system of claim 28c, wherein the sensors are operatively connected to a PID (proportional integral derivative) controller providing feedback control of gases.

29. The cell culture and tissue engineering system of any one of claims 4 to 28, wherein a cold thermal assembly forms the rear of the inner shell body and generates and controls the cold zone airflow path surrounding the reagent fluid reservoir for enhanced reagent stability.

30. The cell culture and tissue engineering system of claim 29, wherein said cold thermal assembly comprises a cold sink array that comprises a plurality of cold sinks compressed with a peltier device to a hot sink for transfer of heat to the hot sink.

31. The cell culture and tissue engineering system of claim 30, wherein compression is spring compression utilizing a Peltier solid-state device comprising an array of spring compression bolts each comprising coil springs, the hot sink acting as a heat conductive path for heat removal.

32. The cell culture and tissue engineering system of claim 31, wherein said Peltier solid-state device functions to pump heat from the cold sinks to the hot sink for subsequent heat transfer to an ambient environment.

33. The cell culture and tissue engineering system of any one of claims 30 to 32, wherein each cold sink array is segmented into functional units comprising a cold sink and associated axial fan.

34. The cell culture and tissue engineering system of claim 33, wherein the axial fan has an axial flow configuration.

35. The cell culture and tissue engineering system of claim 33 or 34, wherein the cold sink comprises a vertical fin structure.

36. The cell culture and tissue engineering system of any one of claims 29 to 35, further comprising thermal insulation to inhibit heat from returning to the cold sink from the hot sink.

37. The cell culture and tissue engineering system of any one of claims 2 to 36, wherein said condensation control means comprises a moisture transport material enclosed within a duct connected to the hot sink, the moisture transport material collecting and moving any condensate that may form and that travels down the cold sink and through to the hot sink where it is evaporated.

38. The cell culture and tissue engineering system of claim 37, wherein said condensation control means minimizes and eliminates undesirable microbial contamination from moisture accumulation.
39. The cell culture and tissue engineering system of any one of claims 29 to 38, wherein the cold thermal assembly can be unhinged from the bottom of the inner shell body to hang in an open configuration for cleaning.
40. The cell culture and tissue engineering system of claim 39, wherein the cold sink array and associated axial fan may be uncoupled for cleaning.
41. The cell culture and tissue engineering system of claim 40, wherein the hot sink fan and associated cowling may be unlatched from an upper portion of the inner shell body and raised into an open configuration for cleaning.
42. The cell culture and tissue engineering system of any one of claims 1 to 41, wherein the reagent fluids reservoir is fluidly connected to the bioreactor module via top mounted port connections for mating with ports on an underside of the bioreactor module.
43. The cell culture and tissue engineering system of claim 42, wherein the reagent fluids reservoir further comprises snap tabs for reversible attachment to the bioreactor module.
44. The cell culture and tissue engineering system of claim 43, wherein the reagent fluids reservoir accommodates reagents required for biological processes and accommodates the retention of waste products eliminated from the bioreactor module.
45. The cell culture and tissue engineering system of claim 44, wherein the reagent fluids reservoir comprises a fluid bags container for storing a plurality of separate reagents and for storing the waste products.
46. The cell culture and tissue engineering system of claim 45, wherein said plurality of separate reagents are stored in reagent bags.
47. The cell culture and tissue engineering system of claim 46, wherein the waste products are stored in reagent bags.
48. The cell culture and tissue engineering system of claim 46 or 47, wherein said reagent bags are flexible reagent bags.
49. The cell culture and tissue engineering system of any one of claims 44 to 48, wherein the reagent fluids reservoir further comprises open air ducts located at the top of front and back walls such that the open air ducts are positioned above said reagent bags providing cold airflow directly above the reagent bags.
50. The cell culture and tissue engineering system of claim 49, further wherein the reagent fluids reservoir comprises a roof with downwardly extending baffles to help direct the cold airflow above and across the reagent bags.
51. The cell culture and tissue engineering system of claim 50, wherein said cell culture cassette further comprises a layer of thermal insulation positioned in between said bioreactor module and said reagent fluids reservoir, said layer of thermal insulation insulating against any migration of heat from the bioreactor module.
52. A cell culture cassette comprising:
a bioreactor module having a bottom part attached with a reagents fluid reservoir;
the reagents fluid reservoir comprising a fluids bag container having open air ducts located on front and back walls of the reservoir.
53. The cell culture cassette of claim 52, wherein the fluids bag container comprises a roof and floor, the roof comprising baffles extending downwardly.
54. The cell culture cassette of claim 52 or 53, wherein the cassette further comprises a layer of thermal insulation positioned in between the bottom of the bioreactor module and the roof of the fluids bag container, said layer of thermal insulation insulating against migration of heat from the bioreactor module.
55. The cell culture cassette of any one of claim 53 or 54, wherein the reagents fluid reservoir is attached via port connections positioned on the roof of said fluids bag container and unobstructed by said layer of thermal insulation.
56. The cell culture cassette of claim 55, wherein the reagents fluid reservoir further comprises snap tabs for attaching to the bioreactor module.
57. An automated cell and tissue culture engineering system comprising the cell culture cassette of any one of claims 52 to 56.
57a. The automated system of claim 57, wherein the cassette comprises one or more sensors linked to a logic means.
58. A reagents fluid reservoir for connection to a bioreactor module, the reagents fluid reservoir comprising a fluids bag container having open air ducts located on front and back walls of the reservoir.
59. The reagents fluid reservoir of claim 57, further wherein the fluids bag container comprises a roof and floor, the roof comprising baffles extending downwardly.
60. A cell culture cassette comprising a bioreactor module and a reagents fluid reservoir according to claim 58 or 59.
61. An automated cell culture and tissue engineering system for receiving and operationally supporting an automated cell culture cassette in a more consistently controlled environment for biological processes, the cell culture cassette comprising a bioreactor module and a reagents fluid reservoir, the system comprising:
a warm zone configured for circulating a tangential warm airflow path surrounding the bioreactor module;
a cold zone configured for circulating a tangential cold airflow path surrounding the reagents fluid reservoir; and
a movable thermal barrier assembly for thermally isolating said warm zone from said cold zone upon installation of the cell culture cassette, and for securing the bioreactor module solely within the warm zone and the reagents fluid reservoir solely within the cold zone.
62. A method for maintaining a controlled thermal environment for biological processes within a bioreactor module of a cell culture cassette, the method comprising:
creating and maintaining a distinct high velocity warm airflow at and around the bioreactor module, and simultaneously creating and circulating a distinct cold air flow around and through a reagents fluid reservoir operatively connected to the bioreactor module,
wherein said first airflow and said second airflow are separate and cannot intermingle.

BRIEF DESCRIPTION OF THE DRAWINGS

The following description of typical aspects described herein will be better understood when read in conjunction with the appended drawings. For the purpose of illustrating the invention, there are shown in the drawings aspects which are presently typical. It should be understood, however, that the invention is not limited to the precise arrangements and instrumentalities of the aspects shown in the drawings. It is noted that like reference numerals refer to like elements across different embodiments as shown in the drawings and referred to in the description.

The description herein will be more fully understood in view of the following drawings.

DESCRIPTION OF THE INVENTION

Figure 1:
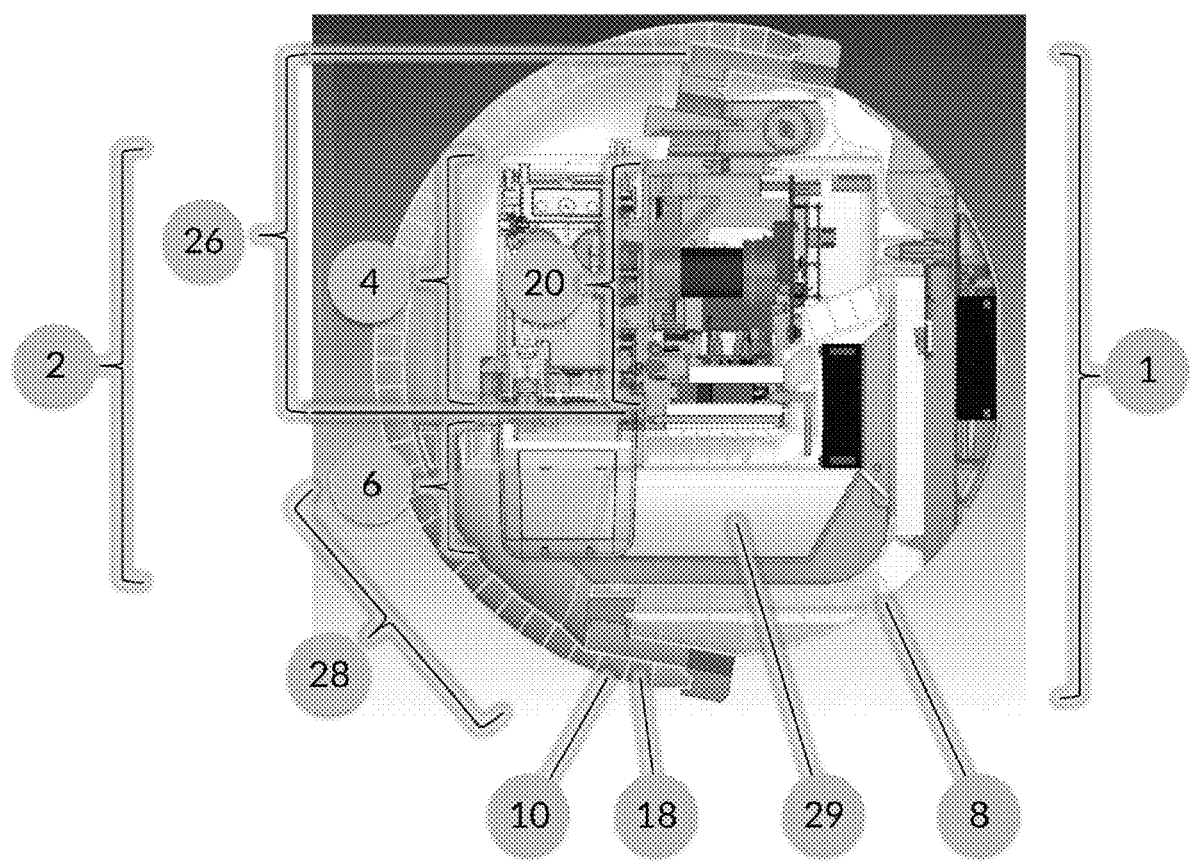
FIG. 1 illustrates a cross section of one embodiment of a cell culture and tissue engineering system of the invention showing a cell culture cassette engaged to operational robotics with the thermal barrier assembly in a locked position.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in the art to which the subject matter herein belongs. As used herein, the following definitions are supplied in order to facilitate the understanding of the present invention.

As used herein, the articles "a" and "an" preceding an element or component are intended to be non-restrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein the terms 'comprises', 'comprising', 'includes', 'including', 'having' and their inflections and conjugates denote 'including but not limited to' and are to be understood to be open-ended, e.g., to mean including but not limited to.

As used herein, the term "about" refers to variation in the numerical quantity. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

It will be understood that any component defined herein as being included may be explicitly excluded from the claimed invention by way of proviso or negative limitation.

As may be used herein the term 'substantially' (or synonyms thereof) denote with respect to the context a measure or extent or amount or degree that encompass a large part or most of a referenced entity, or an extent at least moderately or much greater or larger or more effective or more important relative to a referenced entity or with respect to the referenced subject matter.

As used herein the term 'may' denotes an option or an effect which is either or not included and/or used and/or implemented and/or occurs, yet the option constitutes at least a part of some embodiments of the invention or consequence thereof, without limiting the scope of the invention.

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary.

As used herein "supported", "mounted", "attached", "connected", "joined", "coupled", "linked" may be interchangeably used with respect to the engagement of components of the automated device of the invention. Further, any of these terms may be used with the term "reversibly".

As used herein, "thermal zone" should be understood to be an isolated area that has a defined consistent temperature in terms of being warm or in terms of being cold. Further, the zone having a defined temperature or defined temperature range is maintained at that defined temperature or within the defined temperature range such that that zone is stable, uniform, undeviating or homogenous with respect to the defined temperature or defined temperature range.

As used herein, "warm zone" should be understood to be an isolated confined area with a precise temperature above room temperature (i.e., above about 23° C.). Generally, the precise temperature for mammalian cells is about 37° C. However, depending on the particular needs of the specific cell culture, temperatures above and below 37° C. may still be selected as the precise temperature and accomplished as a "warm zone". For example, stem cells proliferate at 37° C. in the absence of differentiation, if differentiation factors are absent. Conversely, stem cells growing at temperatures above and below 37° C. will differentiate without differentiation factors being present. Furthermore, different "warm zone" temperatures may be required for application of temperature stress on a given culture. The "warm zone" will contain a high velocity warm airflow path. One of skill in the art will understand the meaning of "high velocity" compared to regular airflow velocity. The "warm zone" houses the bioreactor module and has a distinct gas regulating means.

As used herein, "cold zone" should be understood to be an isolated confined area with a temperature range of about 2° C. to 8° C. The exact temperature of the "cold zone" need not be precise but rather an overall temperature reduction such as about 2° C. to 8° C. The "cold zone" contains a cold airflow. The "cold zone" houses the fluids reagents reservoir and any further fluid reagents bags. The "cold zone" houses the condensation control means.

The "warm zone" is separate from the "cold zone" such that the temperature in either zone does not migrate into the other zone. The high velocity warm airflow does not intermingle with the cold airflow.

The cell culture cassette resides in the warm zone.

The reagents fluids reservoir resides in the cold zone.

External (additional) fluid bags reside in the cold zone.

As used herein, "resides" with respect to the "warm zone" or the "cold zone" means that the noted structural element is only subjected to the atmosphere in that particular zone in the closed operation of the culture system.

A general non-limiting overview of the invention and practising the invention is presented below. The overview outlines exemplary practice of embodiments/aspects of the invention, providing a constructive basis for variant and/or alternative and/or divergent aspects/embodiments, some of which are subsequently described.

Figure 2:
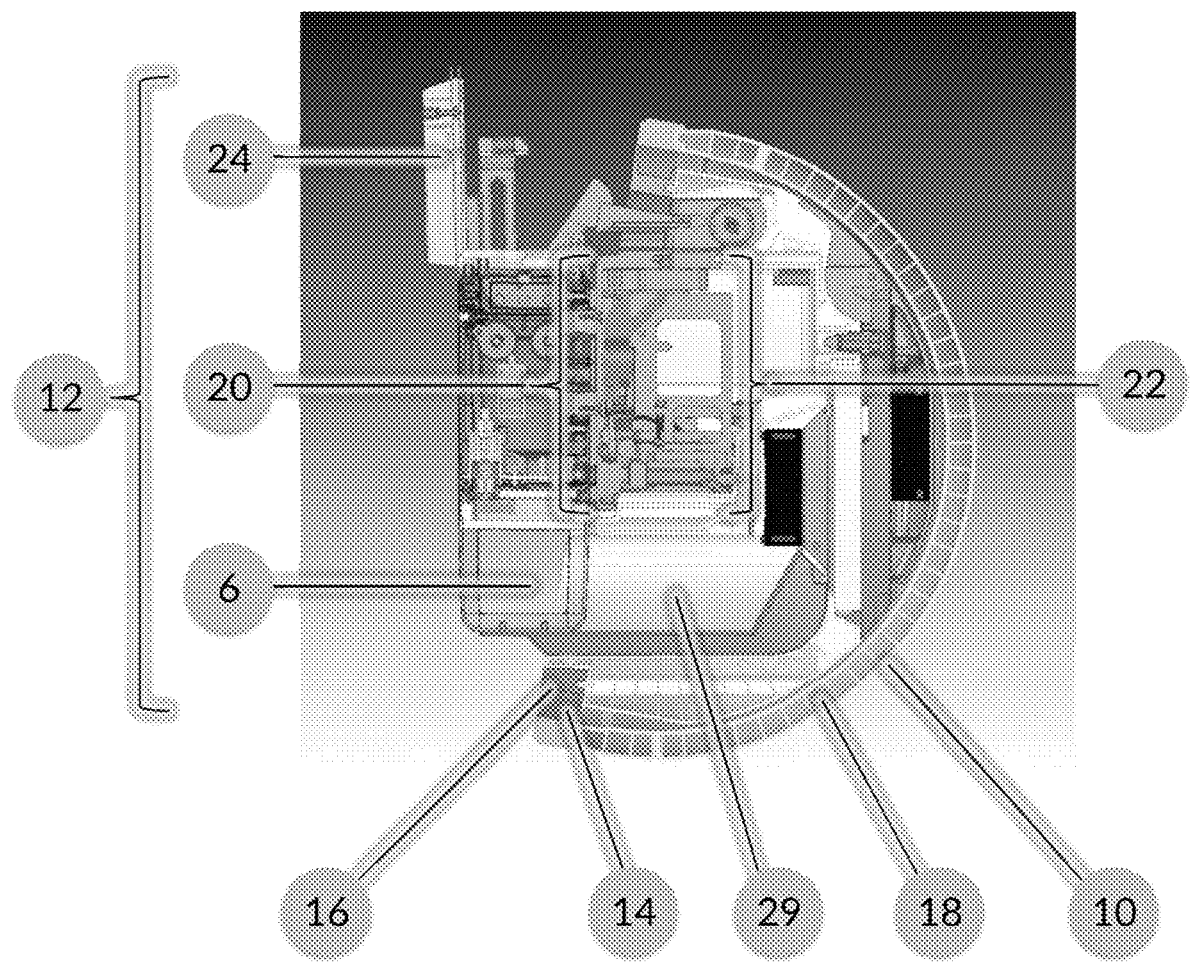
FIG. 2 illustrates a cross section of the system in an open configuration exposing the cell culture cassette that is shown with the thermal barrier assembly in an unlocked position.

FIGS. 1 and 2 show an embodiment of the system of the invention in a closed and open configuration, respectively. FIG. 1 illustrates an embodiment of a cell culture and tissue engineering system 1 of the invention in which a disposable cell culture cassette 2 is installed and operated under automated conditions. The cell culture cassette 2 comprises a bioreactor module 4 and attached reagents fluid reservoir 6. The system 1 resembles a "cocoon-shape" and comprises an inner shell body 8 and an outer shell cover 10 that covers an opening 12 of the inner shell body. The outer shell cover 10 envelops the front opening 12 of the inner shell body and is connected to the inner shell body 8 via a rotatable connection (not shown) at both sides of the inner shell body so that the outer shell cover 10 can rotate to open along the outer arc shape of the inner shell body from a first closed position to an open position rotating about the connection points until the outer shell cover nests the inner shell body (shown in FIG. 2). The front opening 12 of the inner shell body 8 comprises a periphery 14 with a U shaped channel 16 that comprises an inflatable seal 17 such that when the system is closed the inflatable seal is actuated to inflate and engage with an inside surface of the outer shell body to seal the system in an airtight manner. The outer shell cover 10 comprises thermal cells 18 that act as an external thermal barrier.

The cell culture cassette 2 is installed against an operational robotics interface 20 positioned within the opening 12 of the inner shell body 8. The operational robotics interface 20 further comprises associated robotics and electronics 22 within the inner shell body. The cell culture cassette 2 is operationally restrained against the operational robotics interface 20 and locked in this position by a movable thermal barrier assembly 24 that extends from the cell culture cassette 2 to the outer shell cover 10. Locking the cell culture cassette 2 to the operational robotics interface 20 by the movable thermal barrier assembly 24 creates an upper warm zone 26 and a lower cold zone 28. The bioreactor module 4 is secured within the warm zone 26. The reagents fluid reservoir is secured within the cold zone 28. An additional external cold reservoir 29 is located within the cold zone and adjacent to the reagents fluid reservoir of an installed cell culture cassette. This external cold reservoir 29 may contain an additional reservoir bag(s) for collection of fluid waste and/or provide additional required culture fluid(s) and reagent(s). Thus the cell culture system provides both a warm, incubated environment suitable for biological processes (e.g. about 37° C.+/−5° C.) and a separate cold environment for enhanced reagent stability during the period of reagent storage (e.g. over 0° C. to about 10° C.).

In FIG. 2 the system 1 is in an open configuration that exposes the cell culture cassette 2 for inspection and/or removal and further shows the movable thermal barrier assembly 24 in an open raised position. The bioreactor module 4 of the cell culture cassette 2 is fluidly connected to the reagent fluids reservoir 6 via mated port connections (not shown). The bioreactor module 4 supports the operational requirements of a biological process, such as cell culture or tissue engineering and comprises one or more bioreactors that may be operatively connected in series. The reagent fluids reservoir 6 substantially accommodates and stores the reagents required for the biological processes occurring in the one or more bioreactors of the bioreactor module. The reagent fluids reservoir 6 comprises multiple flexible reagent bags (not shown), each of the reagent bags containing one or more of culture medium, growth factors, pharmaceutical agents, cell labels and waste products eliminated from the bioreactor module.

In operation, the outer shell cover 10 is rotated to an open position to enable access to the cassette 2 for installation or removal of the cell culture cassette that is restrained against the operational robotics interface 20 by way of the structural configuration of the movable barrier assembly 24. When cell culture cassette installation/removal is required, the movable thermal barrier assembly 24 can be raised away from the cassette by way of an internal linkage mechanism permitting full access to the cell culture cassette. Following installation of a cassette 2, the thermal barrier assembly 24 is moved to the engaged (lowered) position as shown in FIG. 1, thereby ensuring accurate alignment with the robotics 7 and related interface connections and forming separate warm and cold zones. When the cell culture cassette is installed and the movable thermal barrier is locked in place, the thermal barrier effectively forms part of the lower surface of the warm zone around the cassette and the upper surface of the cold zone around the cassette.

Figure 3A:
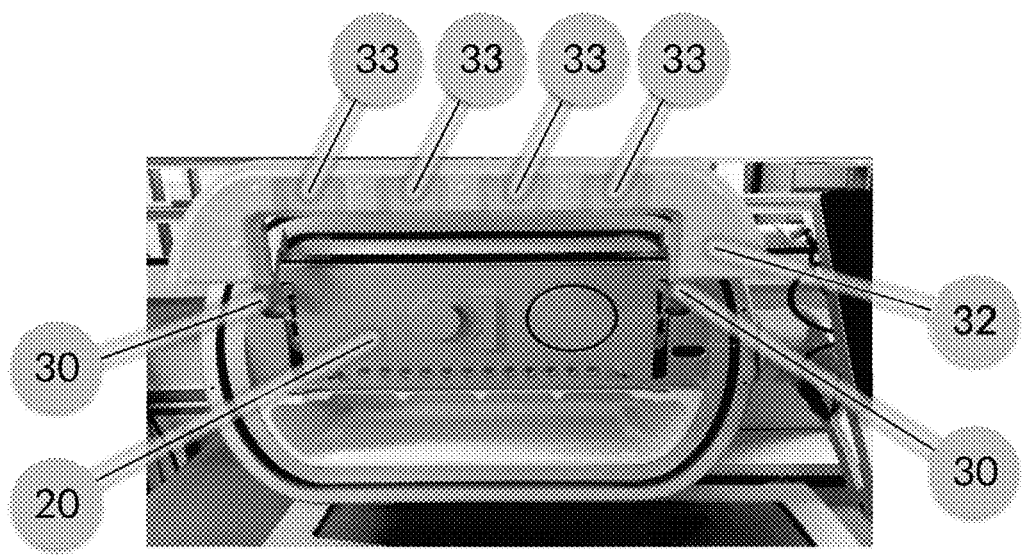
FIG. 3A illustrates a front elevational view of the system showing the operational robotics interface with the thermal barrier assembly in an upright position for installation of a cell culture cassette.
Figure 3B:
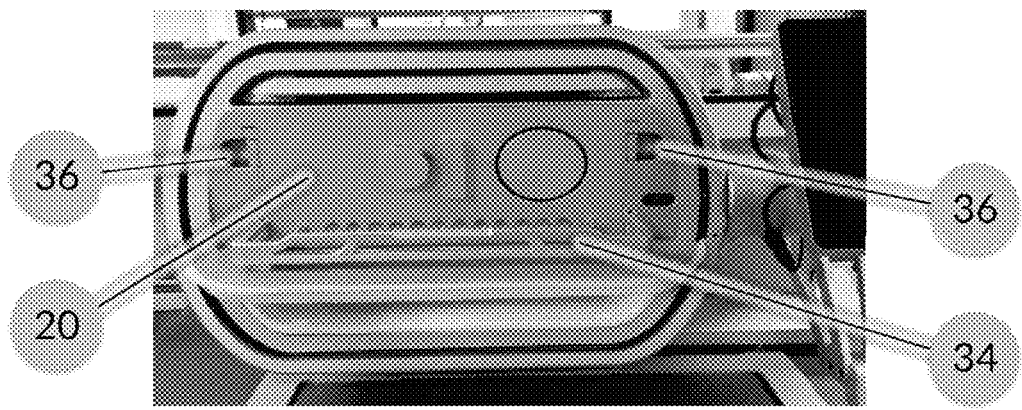
FIG. 3B illustrates a front elevational view of the system of FIG. 3A with the thermal barrier assembly in a locked position.

FIGS. 3A and 3B show a front elevational view of the operational robotics interface 20 with the movable thermal barrier assembly 24 in an open raised position. The operational robotics interface 20 comprises several valve actuators and peristaltic pump connections to which the cell culture cassette is aligned and connected with. The movable thermal barrier assembly 24 comprises levered spaced apart arms 30 that are connected at either side of the operational robotics interface 20 that support a thermal platform 32 shown in the raised position. The underside of the thermal platform is shown to have channels 33. In FIG. 3B the thermal platform 32 is shown with its associated upper handrail 34 that closely conforms to the dimension of an installed and locked cell culture cassette. Recesses 36 are provided adjacent the levered arms 30 that provide operator controlled access to open and extend the movable thermal barrier assembly 24. The upper handrail 34 provides a gripping means for a user to lock the cell culture cassette into position for operation or to unlock and raise the thermal platform 32. The thermal platform 32 is shown to extend forward and radiate around the cell culture cassette to the outer shell cover (shown in FIG. 1). The thermal platform has both a flexible outer seal at its front outer boundary to accommodate relative motion between the thermal platform and the outer shell cover (not shown) and a flexible inner seal that is directly adjacent the cell culture cassette (not shown) to accommodate mounting tolerances of the cell culture cassette. Both seals are elastomeric and impermeable to moisture and vapour.

Figure 3C:
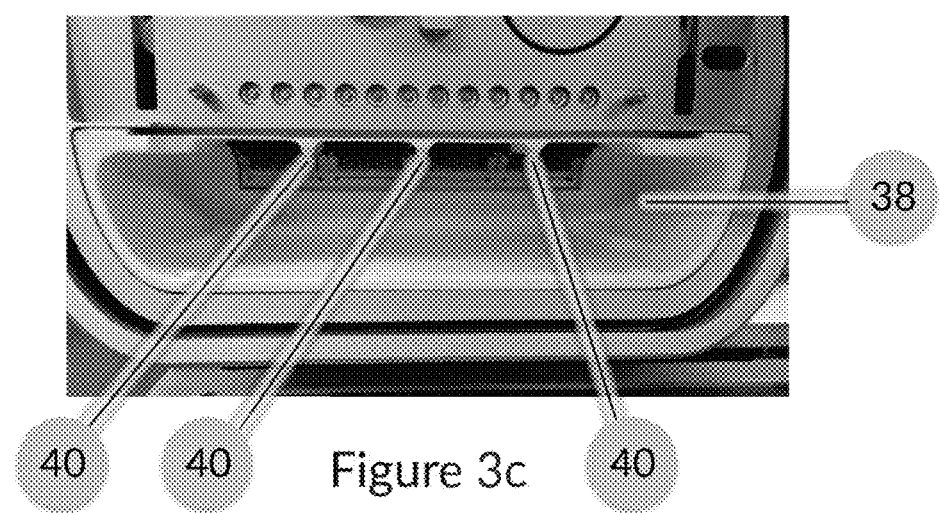
FIG. 3C illustrates a close up front elevational view of the external cold reservoir that forms part of the cold zone and is located adjacent an installed reagent fluid reservoir, the external cold reservoir has baffles for ensuring air return to the cold sink is not blocked. These baffles align with the underlying structure of the thermal barrier assembly seen in FIG. 3B.

FIG. 3C shows the inside of the external cold reservoir 38 that has baffles 40 to help prevent blocking of the air return to the cold thermal assembly shown at the back of the external cold reservoir. The external cold reservoir 38 is positioned adjacent to the reagents fluid reservoir and both are located within the cold zone 28. The refrigeration space may contain separate external reservoir bag(s) outside of the reagents fluid reservoir (not shown). The baffles 40 act to prevent that any reservoir bag contained in the external cold reservoir does not close off the return air back to the cold sink. When the thermal platform is in the lowered locked position around the cell culture cassette the underside channels 33 line up with the baffles 40 to create a continuous structure for the unobstructed cold air flow.

Figure 4:
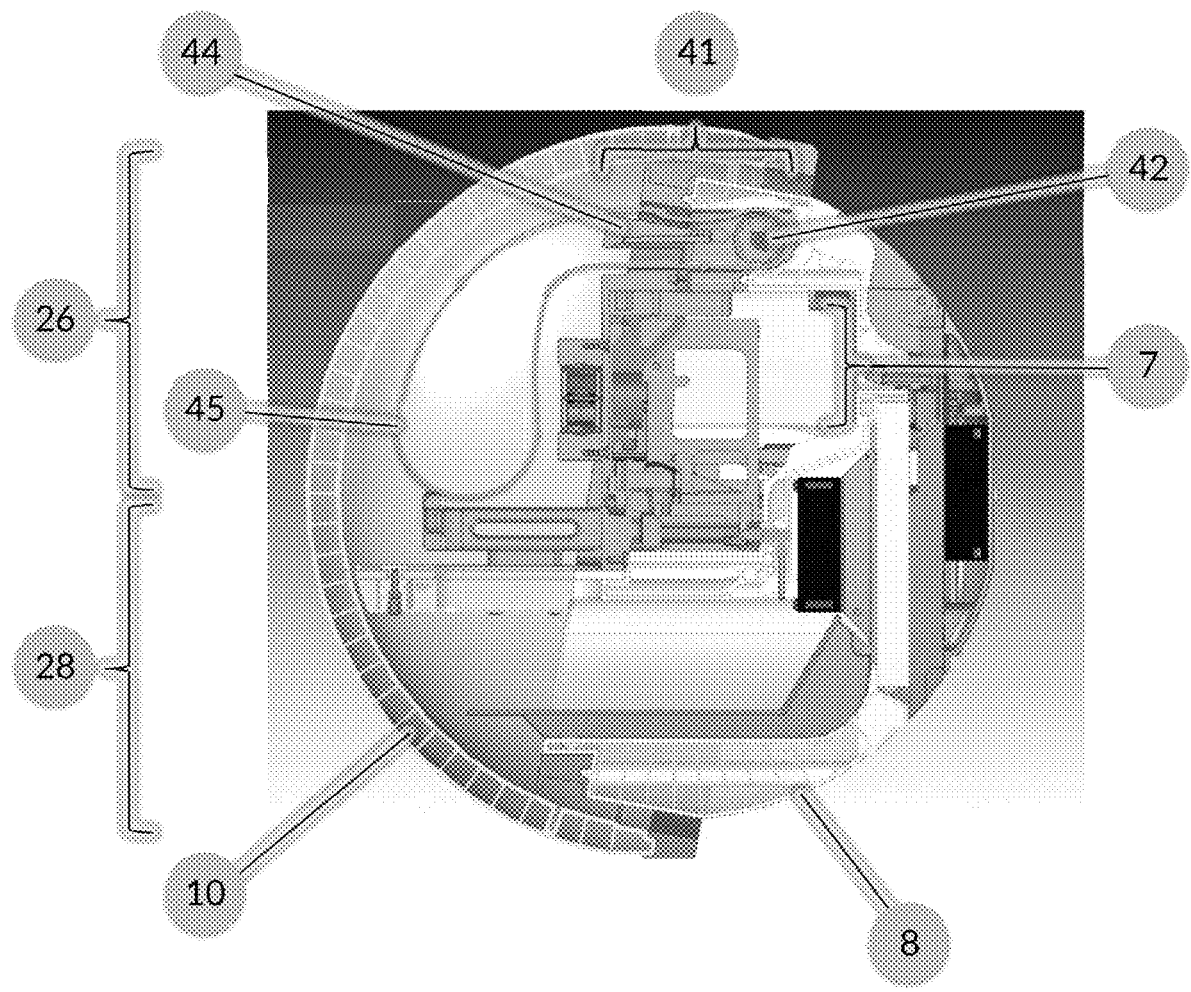
FIG. 4 illustrates the warm zone airflow path and features of the heating assembly.

FIG. 4 shows the temperature-controlled warm zone 26 and cold zone 28 of the cell culture system 1. The system 1 is shown in the closed position. The warm zone has a substantially segregated gas environment to that of the cold zone. The warm zone comprises a system of gas control for gases such as oxygen, carbon dioxide and nitrogen. Nitrogen drives the concentrations of oxygen and/or carbon dioxide below ambient. The warm zone 26 is created by a heating assembly 41 located in an upper section of the inner shell body. The heating assembly comprises a high capacity linear fan 42 operably connected to a heated airflow director 44 to generate and direct a high warm airflow path 45 (shown via arrows) to circulate around the bioreactor module 4. The high capacity linear fan provides for high velocity airflow to minimize spatial and temporal temperature inhomogeneity within the warm zone. The linear fan 42 has a flow configuration that provides a high velocity airflow rate due to the combination of laminar flow, minimal pressure drop and minimal airflow directional changes. The high airflow velocity promotes temperature uniformity due to high convective heat transfer, which inherently minimizes differences in surface temperatures arising within the warm zone from competing thermal sources.

Further, continuous circulation of the high velocity warm airflow is aided by the arc shape of the inside wall of outer shell cover and helps the circular path of the warm high velocity airflow to be consistent and homogeneous. The warm zone is shown to be completely thermally separated from the cold zone. Competing thermal loads are placed on the warm zone by heat transfer with other regions within the cell culture system and by heat transfer to the surrounding ambient environment. The cold zone and typically the ambient environment tend to operate at temperatures below the temperature set point of the warm zone and consequently these factors represent thermal losses for the warm zone. In contrast, specific electronic components within the robotic architecture may operate at temperatures above the temperature of the warm zone and consequently such components represent thermal gains for the warm zone. The configuration and operation of the warm zone obviates problems of heat transfer conditions that inherently drive temperature non-uniformity, such that the uniform warm zone maintains more consistent operating conditions of the biological processes underway within the bioreactor module.

Consistent heating temperatures can be selected for the warm zone as is required by a particular biological process. Controlled temperatures may be selected from 32° C., 33° C., 34° C., 35° C., 36° C., 37° C., 38° C. or more.

Figure 5:
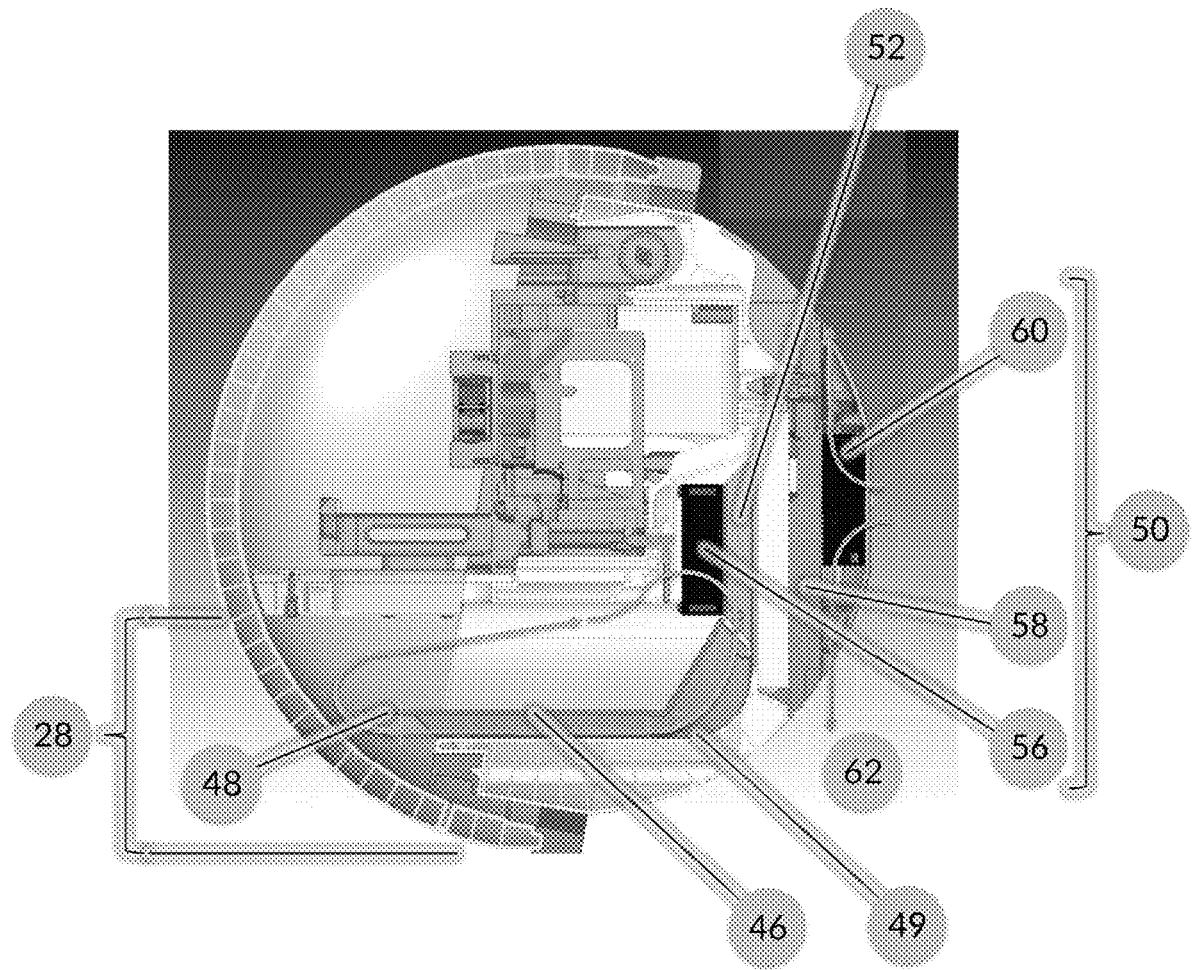
FIG. 5 illustrates the cold zone airflow path and features of the cold thermal assembly.

FIG. 5 illustrates the primary functional components of the cold zone 28. The inner shell body has a floor that supports tray 46 with a forward cantilevered ledge 48 for supporting a bottom surface of the cell culture cassette forming a ducted airflow path below the tray to generate the cold zone airflow path 49 (shown via arrows).

The cold thermal assembly 50 is contained at the rear of the inner shell body to generate and control the cold zone airflow path surrounding the reagent fluid reservoir for enhanced reagent stability. The cold thermal assembly 50 comprises cold sink arrays 52 each comprising a plurality of fin shaped cold sinks 54 (see FIG. 7) that receive heat from the cold zone airflow path via a cold sink fan 56. Peltier solid-state thermoelectric devices (see FIG. 7) transfer heat from the cold sinks 54 to the adjacent hot sink 58. Heat is subsequently rejected from the hot sink to the surrounding ambient air 62 by the hot sink fan 60.

The cold sink fan 56 has an axial flow configuration that provides a high convective heat transfer coefficient due to turbulent flow at the hot sink fins 58 resulting in a minimal temperature difference between the airflow within the refrigerated zone and the cold sink. Reagents within the refrigerated zone and are cooled by virtue of being surrounded by the cold airflow path. Temperatures within the cold zone can be less uniform than in the warm zone, as the key criteria for enhanced reagent stability is overall temperature reduction rather than precise temperature accuracy.

Figure 6:
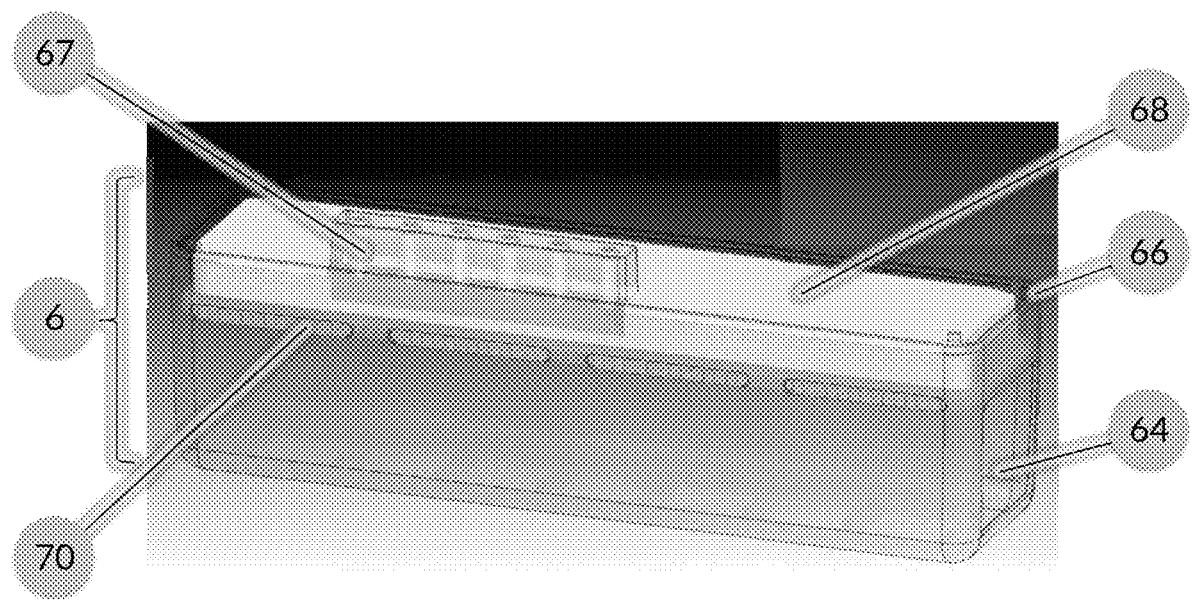
FIG. 6 illustrates a close up perspective view of the reagent fluids reservoir structure.

FIG. 6 illustrates the reagent fluids reservoir 6 that stores multiple reagents in separate fluid containers such as flexible reagent bags (not shown). The reagents bags are constrained within a fluid bags container 64. The reagent fluids reservoir 6 is connected to the bioreactor module via port connections 67 and snap tabs 66 that help to maintain the attachment to the bioreactor module. The reagent bags are insulated against the migration of heat from the warm zone by the cassette thermal insulation 68. The refrigeration temperature of the reagent bags is maintained by the circulation of cold air surrounding and within the reagent fluid reservoir, which includes airflow above the reagent bags via the reagent fluids reservoir open air ducts 70 provided on the front and back walls adjacent the top portion of the reagents fluid reservoir. The top of the reagents fluid reservoir (roof portion) has downwardly extending baffles extending into the reservoir (not shown) that help to direct the cold airflow above and across the reagent bags and allow the airflow to move through to the external cold reservoir guided by the baffles 40 therein to flow unobstructively back to the cold sink array.

The structure of the cold zone is such to create a ducted/channeled airflow therein with minimal obstruction to provide a continuous flow of cold air that will circulate throughout the entire cold zone providing cold airflow underneath and surrounding the reagents fluid reservoir, as well as having the cold air flow penetrate the top portion of the reagents fluid reservoir through the air vents for cold air to flow through the reservoir and directly over the fluids bags and exit through further air vents into the external cold reservoir where it is directed via baffles back to the cold sink of the cold thermal assembly to dispel heat. The provision of channels, baffles, air vents, thermal insulation and the seals and underside channels of the thermal platform together ensure that the cold air is maintained in the cold zone with minimal obstruction for the cold air flow in order to remove heat and circulate cold air.

Figure 7:
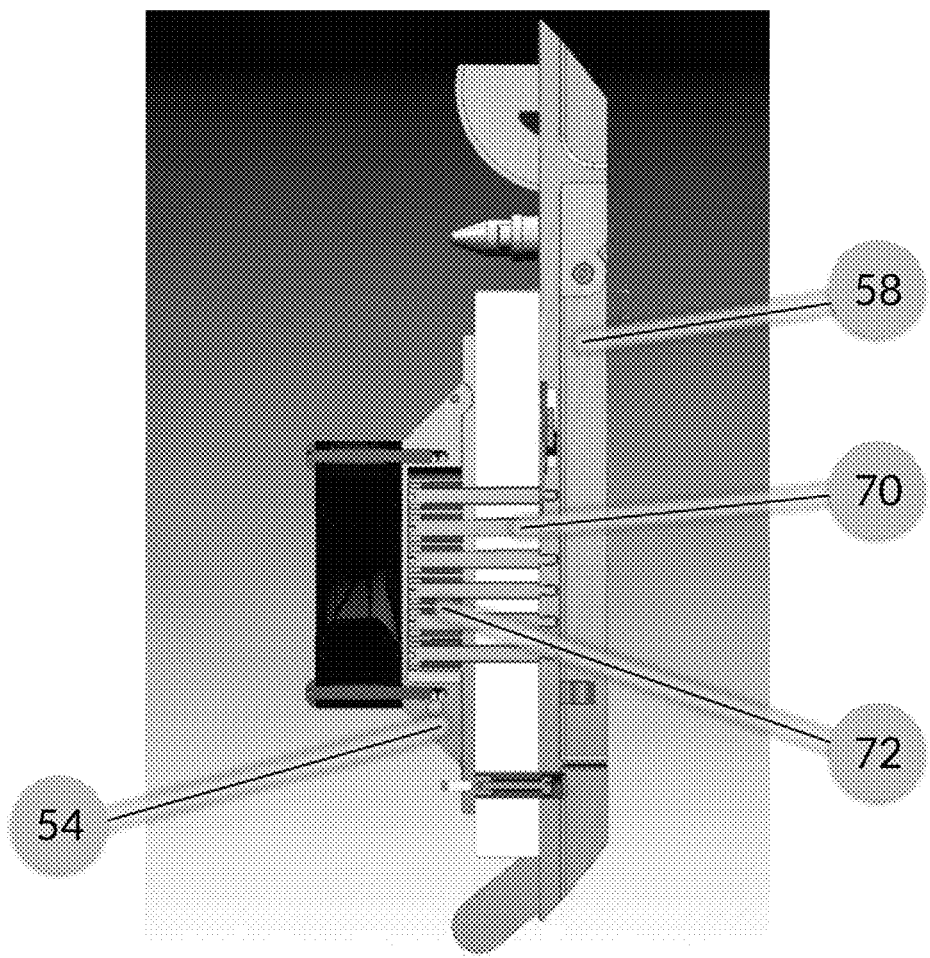
FIG. 7 illustrates a close up cross sectional view of the cold sink array.

FIG. 7 shows the structure of the peltier solid-state thermoelectric devices that pump heat from the cold sink to the hot sink for subsequent heat transfer to the ambient environment. Peltier solid-state devices are preferred over other traditional methods of refrigeration such as vapour compression refrigeration because solid-state devices are compact and have no failure-prone moving parts. Thermal insulation is provided to inhibit heat from returning to the cold sink from the hot sink, as such heat return would compromise thermal effectiveness. The cold sink has an adjacent incorporated monument forming an extension of the cold sink and represents a conductive path for heat to travel from the cold sink to the Peltier solid-state device. The follow-on heat delivered from the Peltier solid-state device to the hot sink is the sum of the heat pumped from the cold sink and electrical power consumed by the Peltier solid-state device. As such, the aggregate heat delivered to the hot sink is significantly greater than the heat removed from the cold sink.

The monument is advantageously incorporated into the cold sink as opposed to the hot sink since less heat transfer is then required through the monument. Consequently, the temperature difference across the monument is significantly less than that present if the monument were located on the hot sink, thereby reducing thermal losses. For Peltier solid-state devices, the coefficient of performance (ratio of heat pumped to electrical power consumed) increases with decreasing temperature differential. Hence the location of the monument on the cold sink provides significant gains in the coefficient of performance relative to the alternative of incorporating the monument as part of the hot sink.

The cold sink array 52 is comprised of multiple individual cold sinks 54 relative to the hot sink 58 that is a monolith. In order to ensure intimate thermal contact between the monument of the cold sink 54, the peltier solid-state device, and the hot sink 58, the cold sinks are segmented into functional units (cold sink plus axial fan), whereby each functional cold sink unit intimately contacts the monolith hot sink (via the Peltier solid-state device) through the use of and array of spring compression bolts 70. The spring compression is achieved through the use of coil springs 72. The key advantage of the spring compression of the cold sink toward the monolith hot sink is that thermal distortions and/or production distortions are self-rectified in that each cold sink assembly can independently align and achieve homogenous compression loads against the associated Peltier solid-state device and onward against the monolith hot sink. Such self-compensating compression loads maximize the effectiveness of individual cold sink thermal transfer to the monolith hot sink.

Figure 8A:
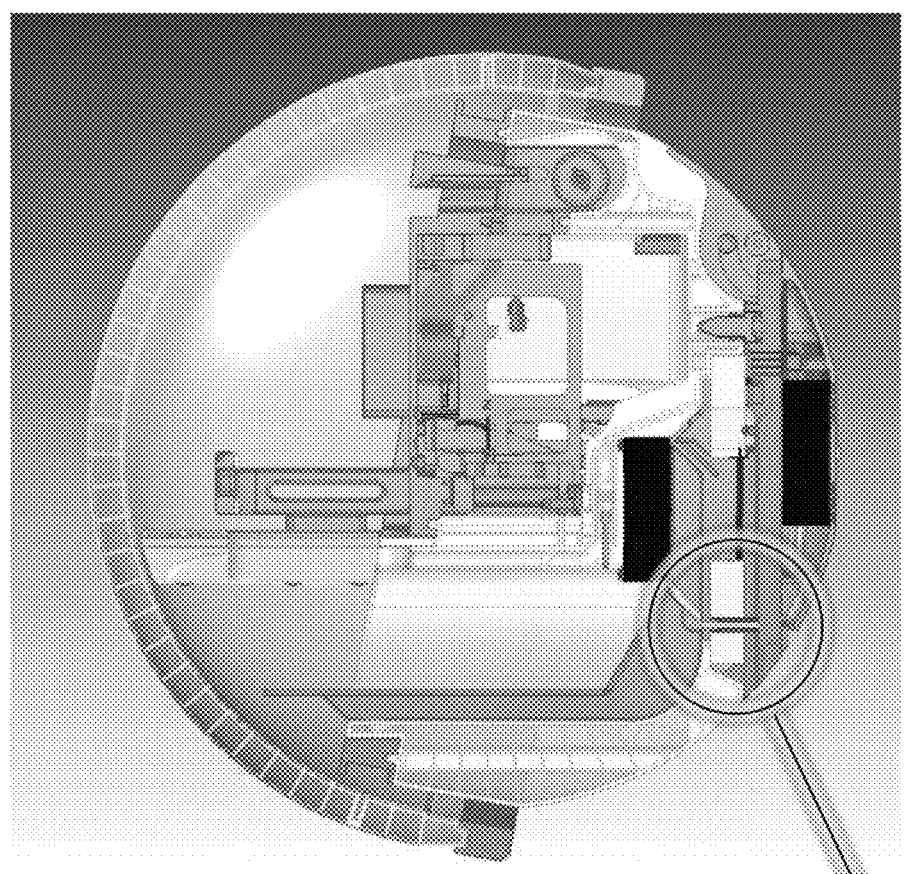
FIG. 8a illustrates the location of the condensation control structure adjacent the cold sink array.
Figure 8B:
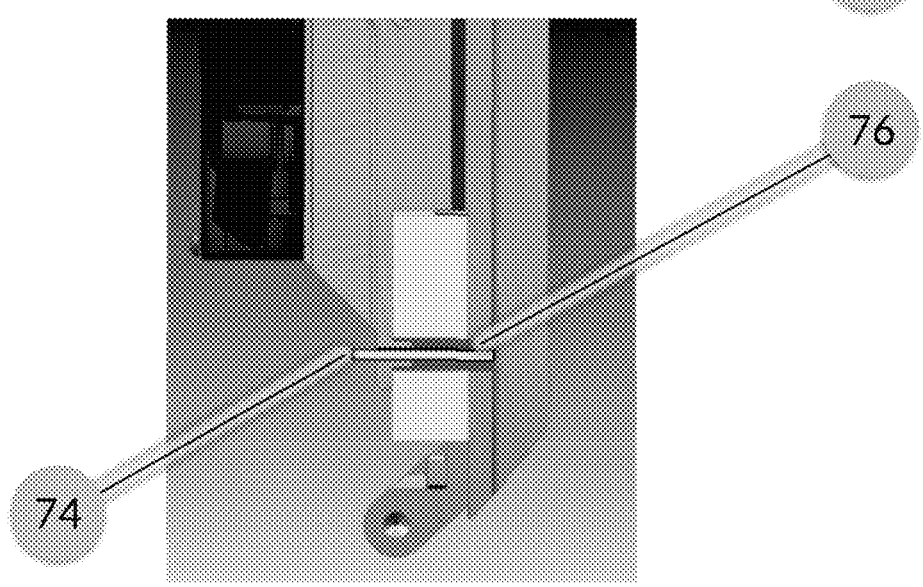
FIG. 8b illustrates an enlarged cross sectional view of the condensation control structure.

When the cell culture system is opened the cold zone inevitably exchanges air with the ambient environment. As a result, when the cell culture system is subsequently closed, air from the ambient environment is entrained within the cold zone. Moisture from the air of the environment condenses if the humidity of the incoming ambient air results in a dew point that is above the ultimate temperature of the cold zone. The resulting inevitable condensation can generate zones of undesirable moisture accumulation within the cold zone, as such accumulations can lead to a potential site for microbial contamination. Condensation naturally initiates and continues on the cold sink, as the surface of this component is the coldest surface within the refrigeration zone. In order to automatically manage and hence remove the complications of condensation, within the cold zone the cell culture system employs a condensation control mechanism 73 with the location shown in FIG. 8A. Shown more closely in FIG. 8B, the condensation control mechanism 73 comprises a moisture transport material 74. The moisture transport material 74 collects condensate as condensation forms on the cold sink and travels down the fins of the cold sink by the effect of gravity and the action of the airflow downwards over the cold sink fins. The moisture transport material protrudes from the cold sink through a dedicated duct 76 to the hot sink whereupon the transmission of moisture is subsequently and continuously evaporated into the surrounding environment by the heat of the hot sink. This condensation management strategy requires no moving parts or extra power.

Figure 9:
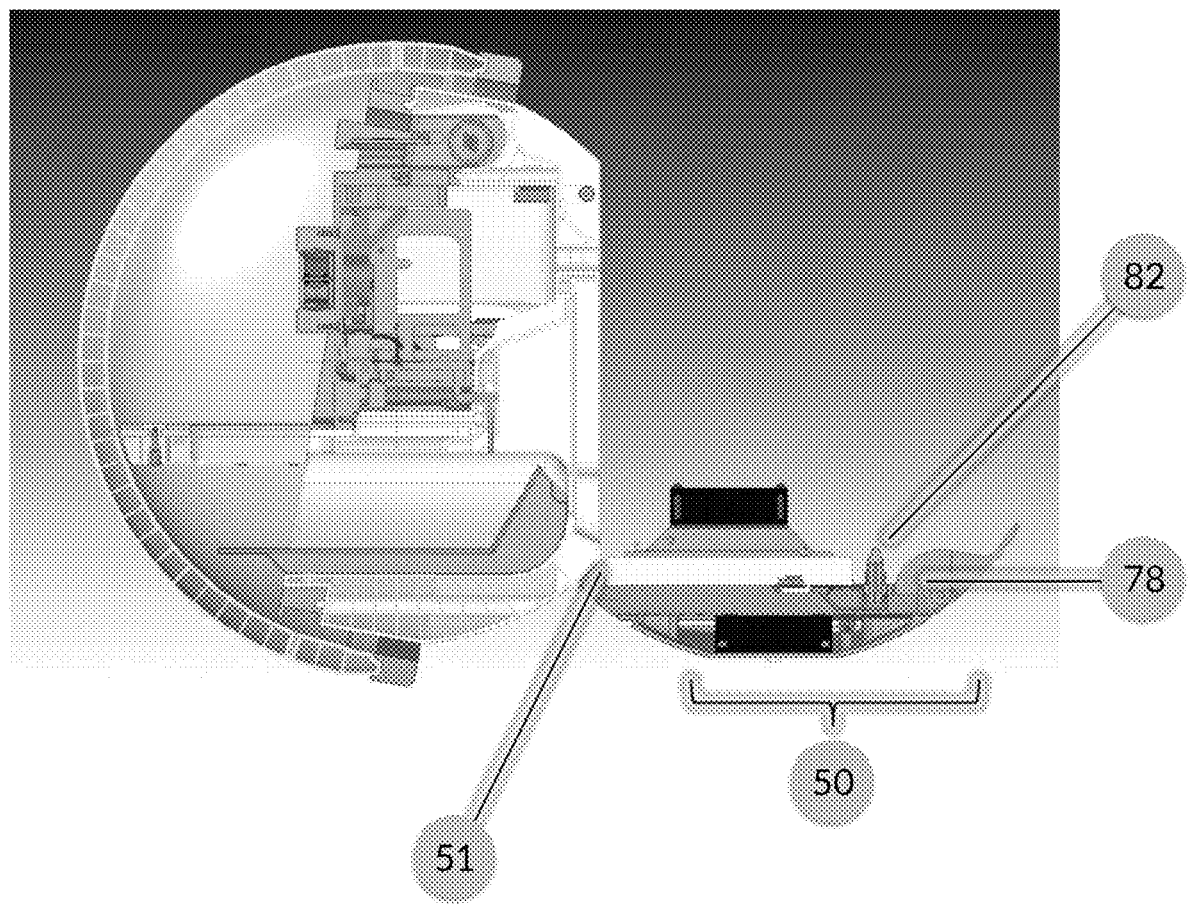
FIG. 9 illustrates the cold thermal assembly unhinged from the system.

Service and cleaning of the cell culture system are required for Good Manufacturing Practice. FIG. 9 shows the cold thermal assembly 50 can be unlatched and supported on a hinge 51 to hang open to enable service and cleaning. The cold thermal assembly is released from the position of regular operation via activation of latch 78 and subsequent downward rotation about hinge points. The refrigeration power connector 82 provides for reliable electrical connections for data and power when the cold thermal assembly is returned to the normal closed operation configuration.

Figure 10:
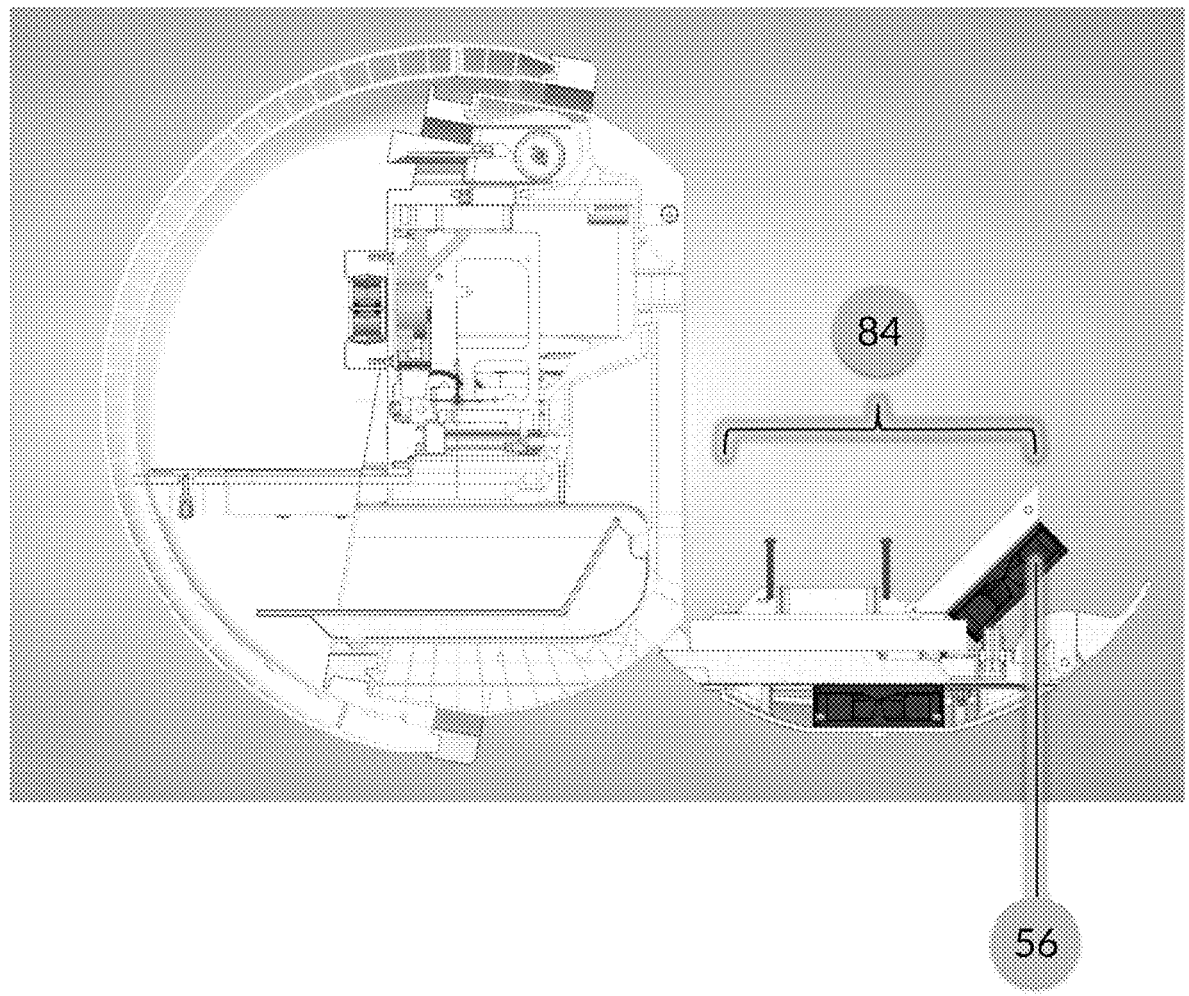
FIG. 10 illustrates the cold thermal assembly with unfastened cold fan.

FIG. 10 further illustrates that the cold sink fan 56 comprises an assembly 84 that can be uncoupled and withdrawn away from the cold sink to enable further detailed cleaning of the underlying cold sink.

Figure 11:
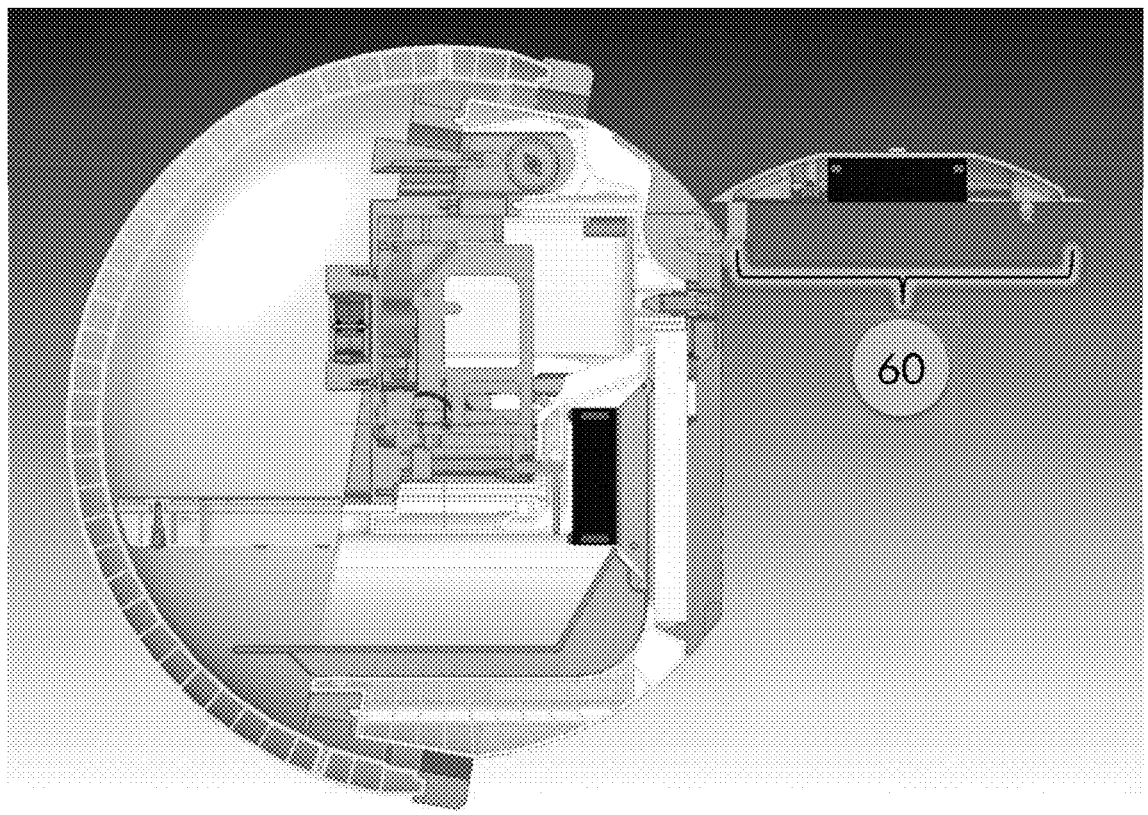
FIG. 11 illustrates the hot sink fan and associated cowling released from the rear of the system.

FIG. 11 further illustrates how the hot sink fan 60 and related cowling may be withdrawn upwardly and away from the hot sink via hinges enabling further detailed cleaning of the underlying hot sink.

In embodiments, the use of a hollow shaft enables connection of the interior of the cell culture system to the exterior of the system, allows for the creation of a unique third control zone within the shaft to enable processes to be run at a temperature other than the culture temperature or the refrigeration temperature. Such an embodiment can be used for process steps that potentially benefit from an intermediate temperature and can be to controlled in this transition zone.

In additional embodiments, a thermal window can be included in the warm and/or cold zones comprised of twin liquid crystal (LCD) windows (or functional equivalent) incorporated into the outer shell which permit: viewing of internal cassette actions when the LCD is transparent; opacity to harmful light degradation of reagent when the LCD is activated and opaque; and a thermal barrier due to twin LCD walls forming an entrapped air space.

In embodiments, the separate internal airflows can be linked to centralized airflow management system capable of controlling multiple production units.

In additional embodiments, air filtration can be included within the air circulation paths and such filter being disposable following each treatment or other reasonable period.

It is understood by one of skill in the art that where feasible, materials for fabrication of components of the system described herein are selected to maximize thermal insulation properties without compromising the primary function of the components with respect to biological compatibility (e.g. non-toxic, USP Class VI compliant) or structural properties (e.g. strength, rigidity, toughness and weight). While the system is shown to be generally configured in a cocoon shape, this may vary, as well as size, so long as the shape maintains the warm and cold airflow paths therein.

Furthermore the cell culture and tissue engineering system of the invention comprises a variety of sensors associated with and/or located within the cold zone, the hot zone, the cell culture cassette, the heating assembly, the cold thermal assembly, and associated with the operational robotics interface and associated internal robotics and electronics and further associated with computer means.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A cell culture system for receiving and operationally supporting an automated cell culture cassette for biological processes,
the automated cell culture cassette comprising a bioreactor module and a reagents fluid reservoir, the system comprising:
a warm zone configured to circulate a warm airflow path surrounding the bioreactor module;
a cold zone configured to circulate a cold airflow path surrounding the reagents fluid reservoir;
a housing having an outer shell cover and an inner shell body, wherein the outer shell cover encloses a front opening of the inner shell body when the system is closed;
an operational robotics interface positioned within the inner shell body; and
a movable thermal barrier assembly having an unlocked, raised position for installing the automated cell culture cassette, and a locked, lowered position for thermally isolating the warm zone from the cold zone, the movable thermal barrier assembly operationally restraining the automated cell culture cassette against the operational robotics interface;
and wherein, when in the locked position, the thermal barrier assembly forms a portion of a lower surface boundary of the warm zone and a portion of an upper surface boundary of the cold zone.

2. The cell culture system of claim 1, wherein the operational robotics interface includes valve actuators, peristaltic pump connectors, and related control systems for mating with corresponding connections on the cell culture cassette.

3. The cell culture system of claim 1, wherein the movable thermal barrier assembly includes a pair of spaced apart arms internally connected at either side of the operational robotics interface that support a central thermal platform with an associated upper handrail.

4. The cell culture system of claim 1, wherein the inner shell body comprises a floor supporting a tray with a forward cantilevered ledge that supports part of a bottom surface of the cell culture cassette.

5. The cell culture system of claim 1, wherein a heating assembly is provided in an upper section of the inner shell body, the heating assembly generating the warm airflow path directed at the bioreactor module.

6. The cell culture system of claim 5, wherein the heating assembly comprises a high-capacity linear fan operably connected to a heated airflow director.

7. The cell culture system of claim 6, wherein the high-capacity linear fan and the heated airflow director generates a consistent and homogenous flow.

8. The cell culture system of claim 5, wherein the heating assembly maintains a substantially uniform temperature throughout the warm zone.

9. The cell culture system of claim 1, wherein a cold thermal assembly in a rear of the inner shell body generates and controls the cold airflow path surrounding the reagents fluid reservoir.

10. The cell culture system of claim 9, wherein the cold thermal assembly includes a cold sink array that includes a plurality of cold sinks compressed with a Peltier device to a hot sink for transfer of heat to the hot sink.

11. The cell culture system of claim 1, wherein the bioreactor module is fluidly connected to the reagents fluid reservoir.

12. The cell culture system of claim 1, wherein the cold zone further includes a condensation control.

13. The cell culture system of claim 1, wherein the cold zone includes a cold reservoir positioned adjacent to the reagents fluid reservoir.

14. The cell culture system of claim 13, wherein the cold reservoir includes at least one baffle.

15. The cell culture system of claim 14, wherein the thermal barrier assembly includes at least one channel, and, when the thermal barrier is in the locked position, the at least one baffle of the cold reservoir is aligned with the at least one channel of the thermal barrier.

* * * * *